(12) United States Patent
Chabot et al.

(10) Patent No.: US 8,546,346 B2
(45) Date of Patent: Oct. 1, 2013

(54) METHODS TO REPROGRAM SPLICE SITE SELECTION IN PRE-MESSENGER RNAS

(75) Inventors: Benoit Chabot, Sherbrooke (CA); Jonathan Villemaire, Sherbrooke (CA); Sherif Abou Elela, Stoke (CA); Faiz-ul Hassan Nasim, Sherbrooke (CA)

(73) Assignee: La Societe de Commercialisation des Produits de la Recherche Appliquee Socpra-Sciences Sante et Humaines S.E.C., Quebec (CA)

( * ) Notice: Subject to any disclaimer, the term of this patent is extended or adjusted under 35 U.S.C. 154(b) by 0 days.

(21) Appl. No.: 12/291,887

(22) Filed: Nov. 14, 2008

(65) Prior Publication Data
US 2009/0186846 A1 Jul. 23, 2009

Related U.S. Application Data

(63) Continuation of application No. 10/524,359, filed as application No. PCT/CA03/00988 on Jun. 30, 2003, now abandoned.

(60) Provisional application No. 60/402,765, filed on Aug. 12, 2002.

(51) Int. Cl.
*C12N 15/11* (2006.01)
*A61K 48/00* (2006.01)
*C12Q 1/68* (2006.01)
*C07H 21/02* (2006.01)
*C07H 21/04* (2006.01)

(52) U.S. Cl.
CPC ..................................... *A61K 48/00* (2013.01)
USPC ...... 514/44 A; 514/44 R; 536/23.1; 536/24.5; 435/6.1

(58) Field of Classification Search
None
See application file for complete search history.

(56) References Cited

U.S. PATENT DOCUMENTS
2002/0068321 A1* 6/2002 Newman et al. ............. 435/69.1

FOREIGN PATENT DOCUMENTS
WO WO2004016787 2/2004

OTHER PUBLICATIONS

Roberts, J. et al (2006) Molecular Therapy vol. 14 No. 4.
Suwanmanee, T. et al (2002) Molecular Pharmacology 62:545-553.
Sazani, P. et al (2002) Nature Biotechnology vol. 20.
Skordis, L, etal, Bifunctional antisense oligonucleotides provide a trans-acting splicing enhancer that stimulates SMN2 gene expression in patient fibroblasts, 2003, PNAS, vol. 100, No. 7, pp. 4114-4119.
Cartegni, L, etal, Correction of disease-associated exon skipping by synthetic exon-specific activators, 2003, Nat. Struct. Bio., vol. 10, No. 2, pp. 120-125.
Shirohzu, H., etal, Repression of Aberrant Splicing in Human β-Globin Pre-mRNA With HbE Mutation by Antisense Oligoribonucleotide or Splicing Factor SF2/ASF, 2000, Intl Jour. of Hemat., pp. 28-33.
Taylor, J, etal, Induction of endogenous Bcl-xS through the control of Bcl-x pre-mRNA splicing by antisense oligonucleotides,1999, Abstract-Nature Biotech. -XP-002262732—pp. 1097-1100.
Lacerra G, etal, Restoration of hemoglobin A synthesis in erythroid cells from peripheral blood of thalassemic patients, 2000, Abstract-PNAS-XP00226733—pp. 9591-9596.
Chabot,B.,etal, An Intron Element Modulating 5' Splice Site Selection in the hnRNP A1 Pre-mRNA mRNA Interacts with hnRNP A1, 1997, Molecular & Cell. Bio-Amer Soc. For Micro., pp. 1776-1786.
Burd,C,etal,RNA binding specificity of hnRNP A1 :significance of hnRNP A1 high-affinity binding sites in pre-mRNA splicing, 1994, EMBO Jour., pp. 1197-1204.
Dickson, Alexa et al (2008), A Negatively Acting Bifunctional RNA Increases Survival Motor Neuron Both In Vitro and In Vivo, Human Gene Therapy, 19:1307-1315.
Astriab-Fisher, A. et al (2002), Conjugates of Antisense Oligonucleotides with the Tat and Antennapedia Cell-Penetrating Peptides: Effects on Cellular Uptake, Binding to Target Sequences, and Biologic Actions, Pharmaceutical Research, 19(6):744-754.
Gendron, D. et al. (2006), Modulation of 5' Splice Site Selection Using Tailed Oligonucleotides Carrying Splicing Signals, BMC Biotechnology,13:6:5.
Caceres, JF et al (2002) Alternative splicing: multiple control mechanisms and involvement in human disease Trends Genet 18(4):186-193.
Cartegni, L et al (2002) Listening to silence and understanding nonsense: exonic mutations that affect splicing Nat Rev Genet 3(4):285-298.
Villemaire, J et al (2003) Reprogramming alternative pre-messenger RNA splicing through the use of protein-binding antisense oligonucleotides J Biol Chem 278(50):50031-50039.

\* cited by examiner

*Primary Examiner* — Dana Shin
(74) *Attorney, Agent, or Firm* — Klauber & Jackson LLC

(57) ABSTRACT

The present invention relates to a method of modulating splice site selection, splicing and alternative, the method comprising the step of hybridizing an oligonucleotide-protein conjugate to a target pre-mRNA molecule in a cell or cell extract, wherein the oligonucleotide-protein conjugate comprises an oligonucleotide moiety which comprises at least two distinct sequence elements: (i) a nucleic acid sequence that is complementary to a specific region upstream of the splice site in the target pre-mRNA molecule; and (ii) an extension containing a protein binding site sequence element for covalently binding a protein; wherein the protein moiety comprises a protein capable of modulating splicing of the splice site upon binding with the protein binding site.

6 Claims, 22 Drawing Sheets

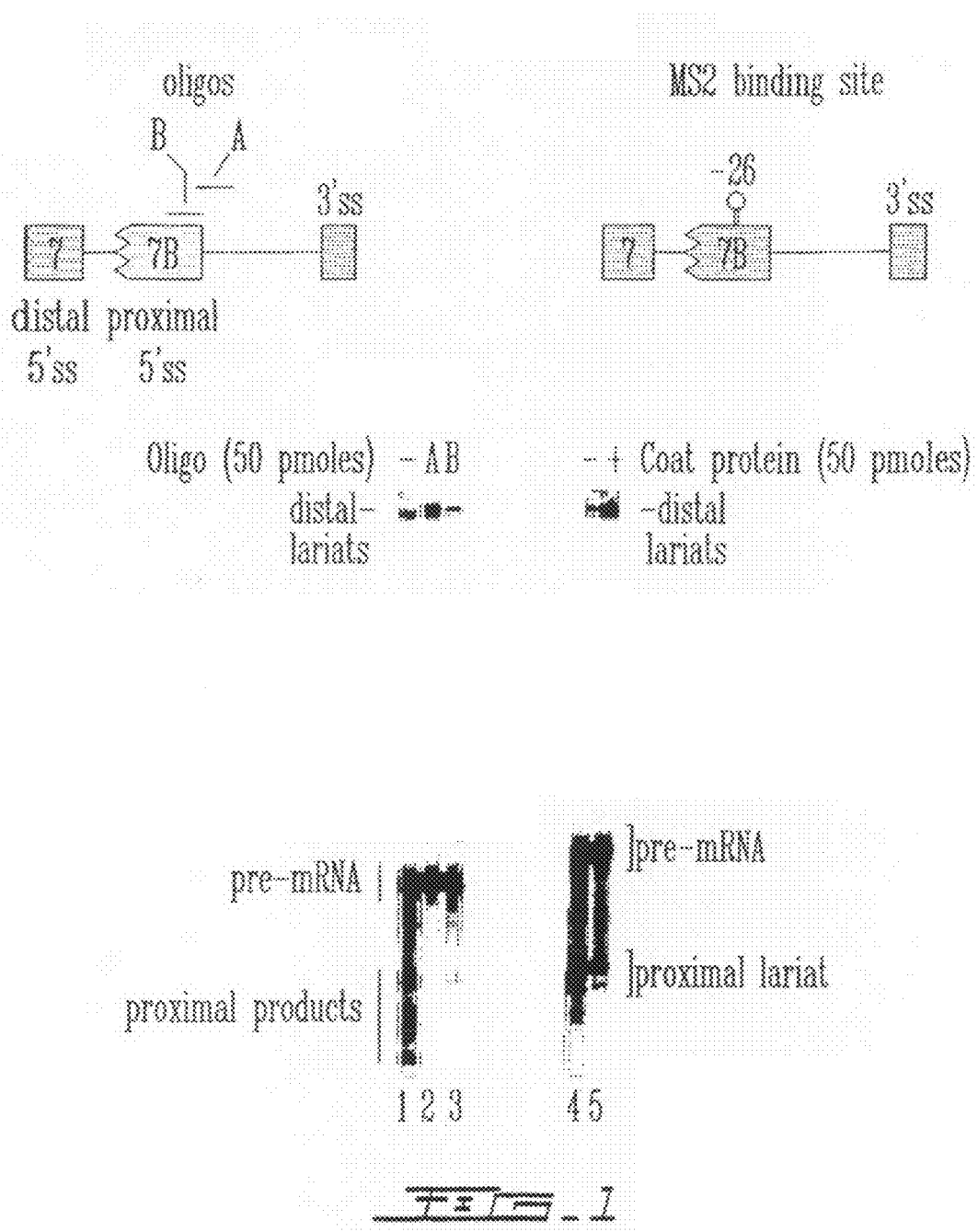

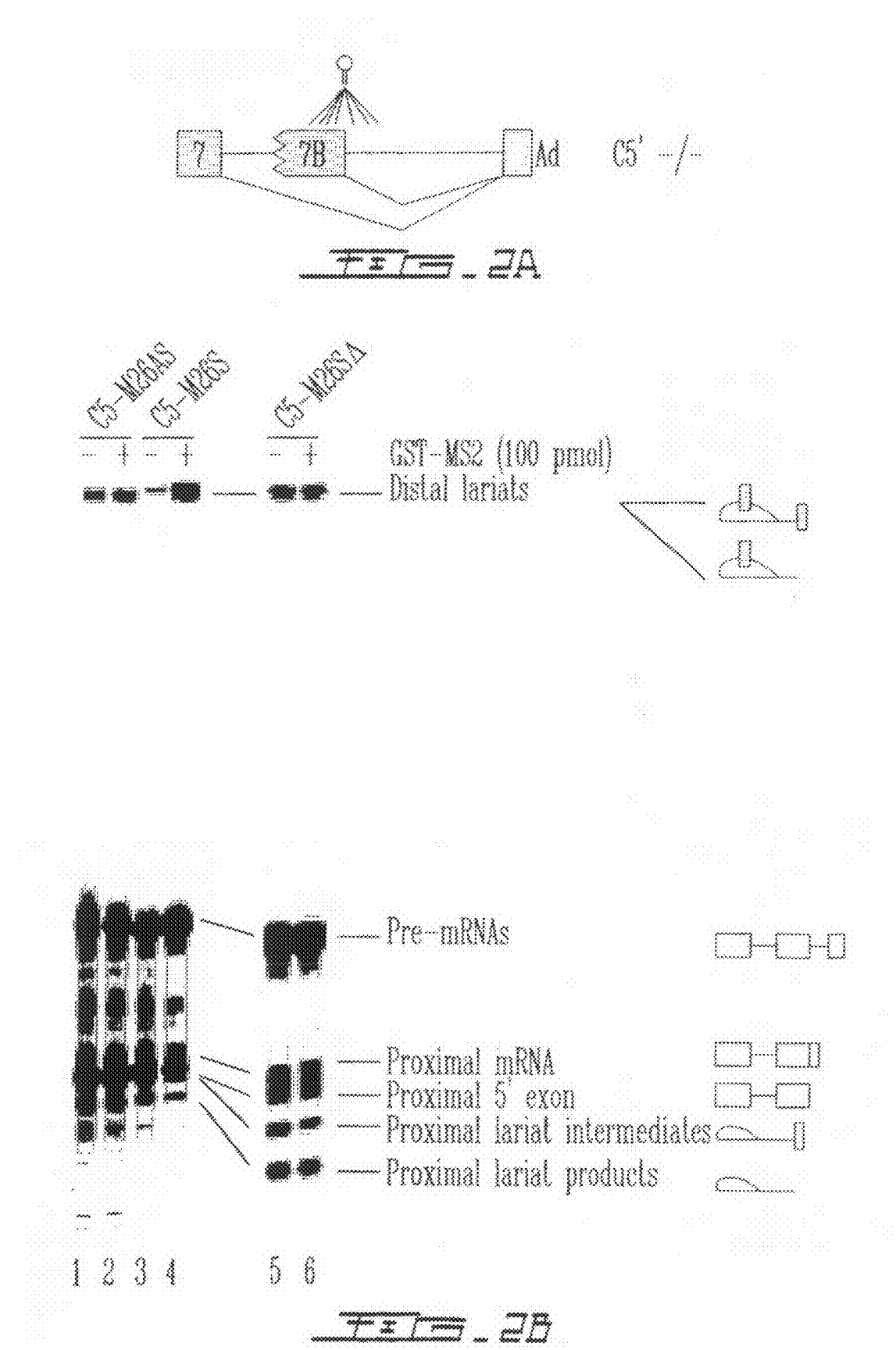

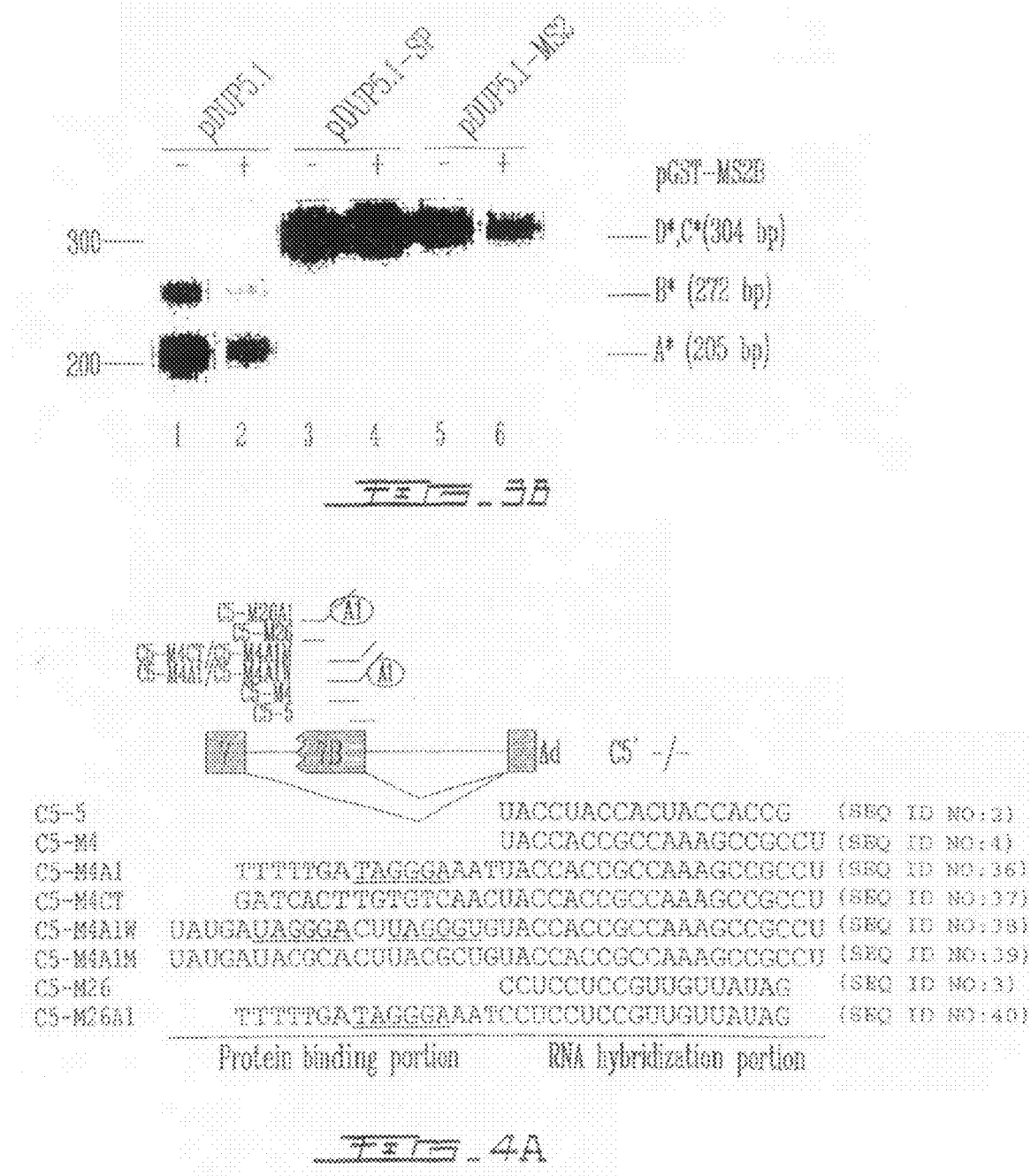

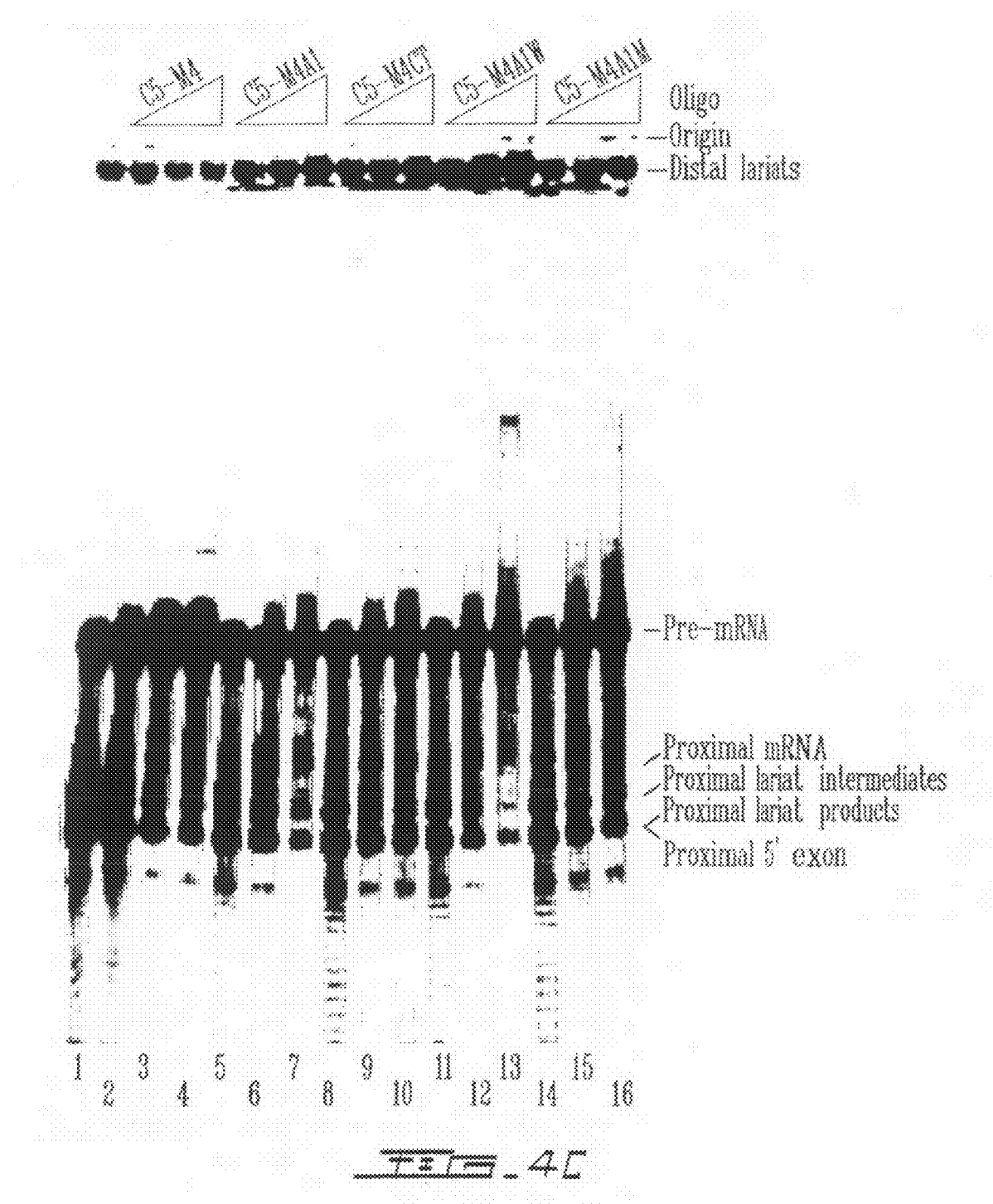

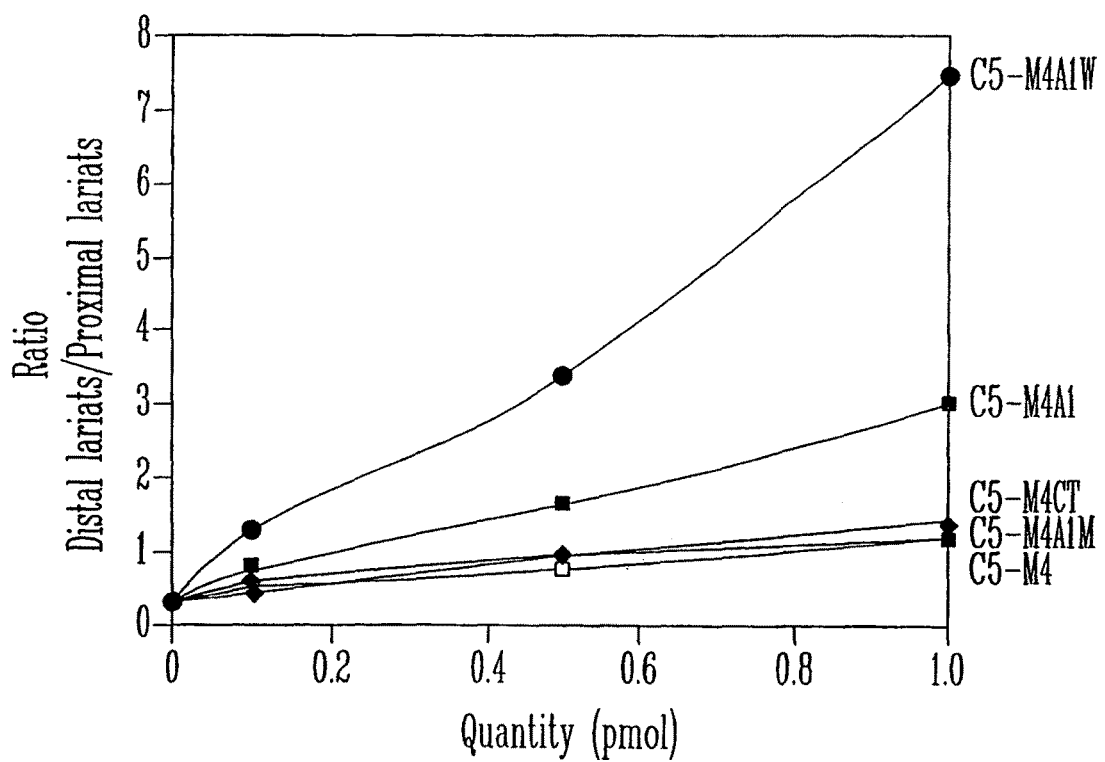
FIG_4D

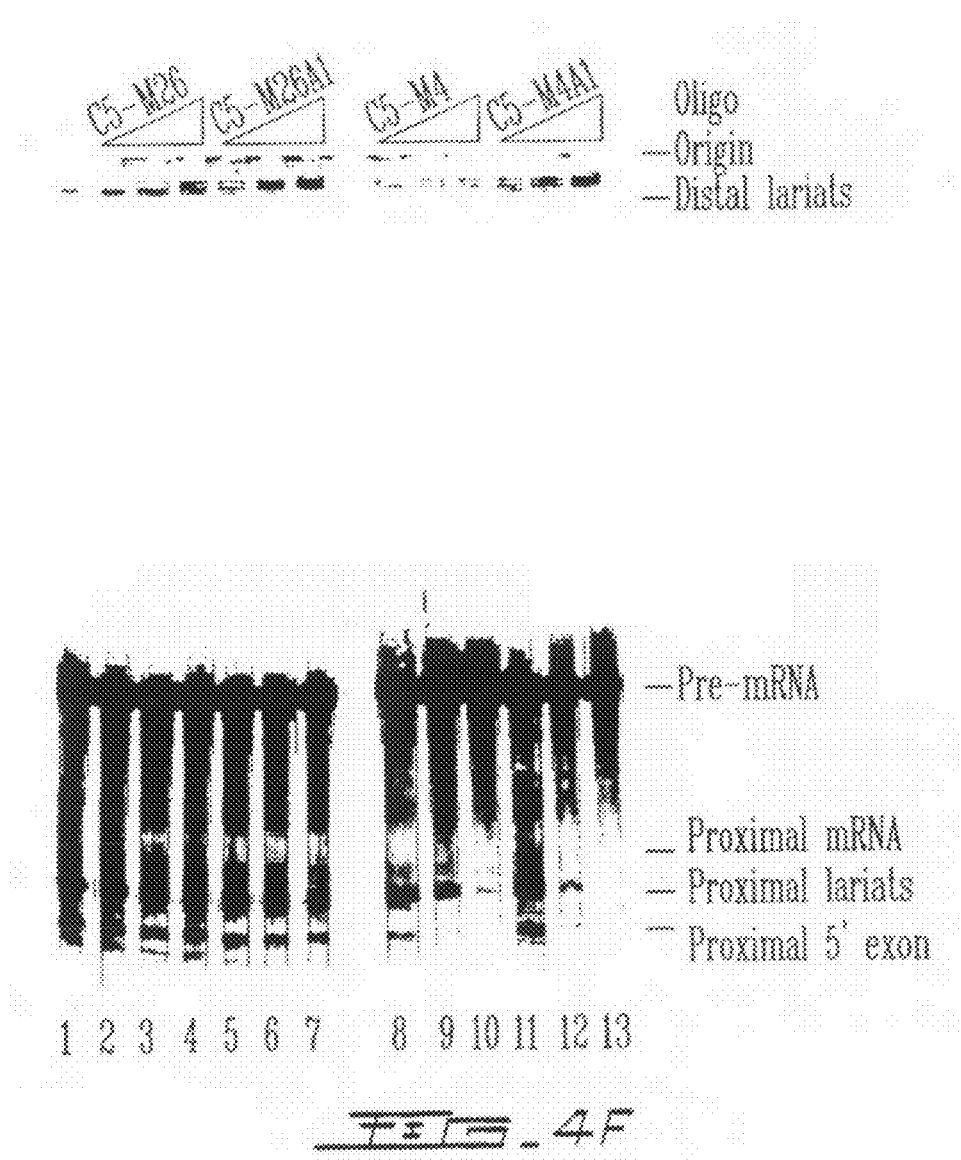

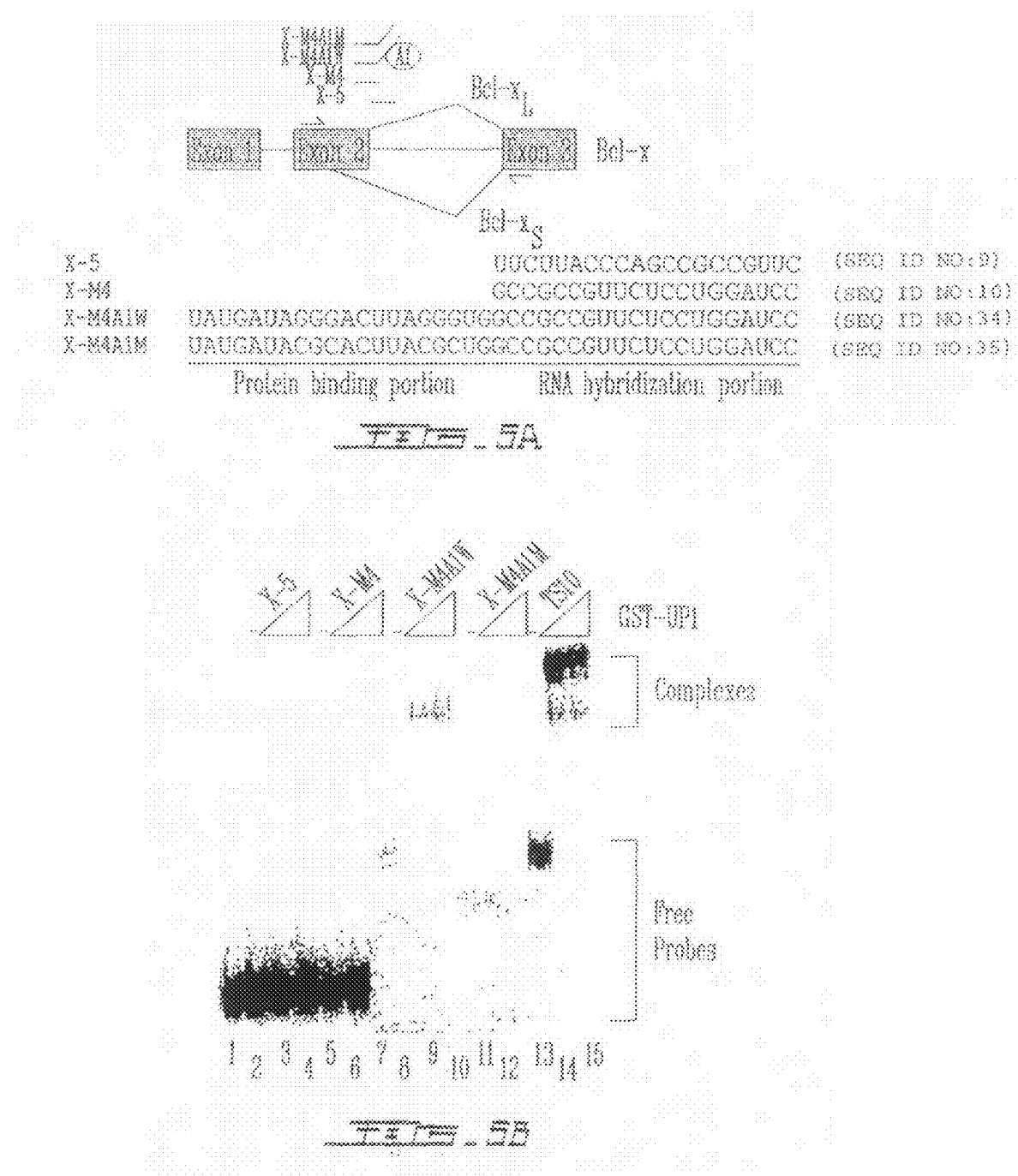

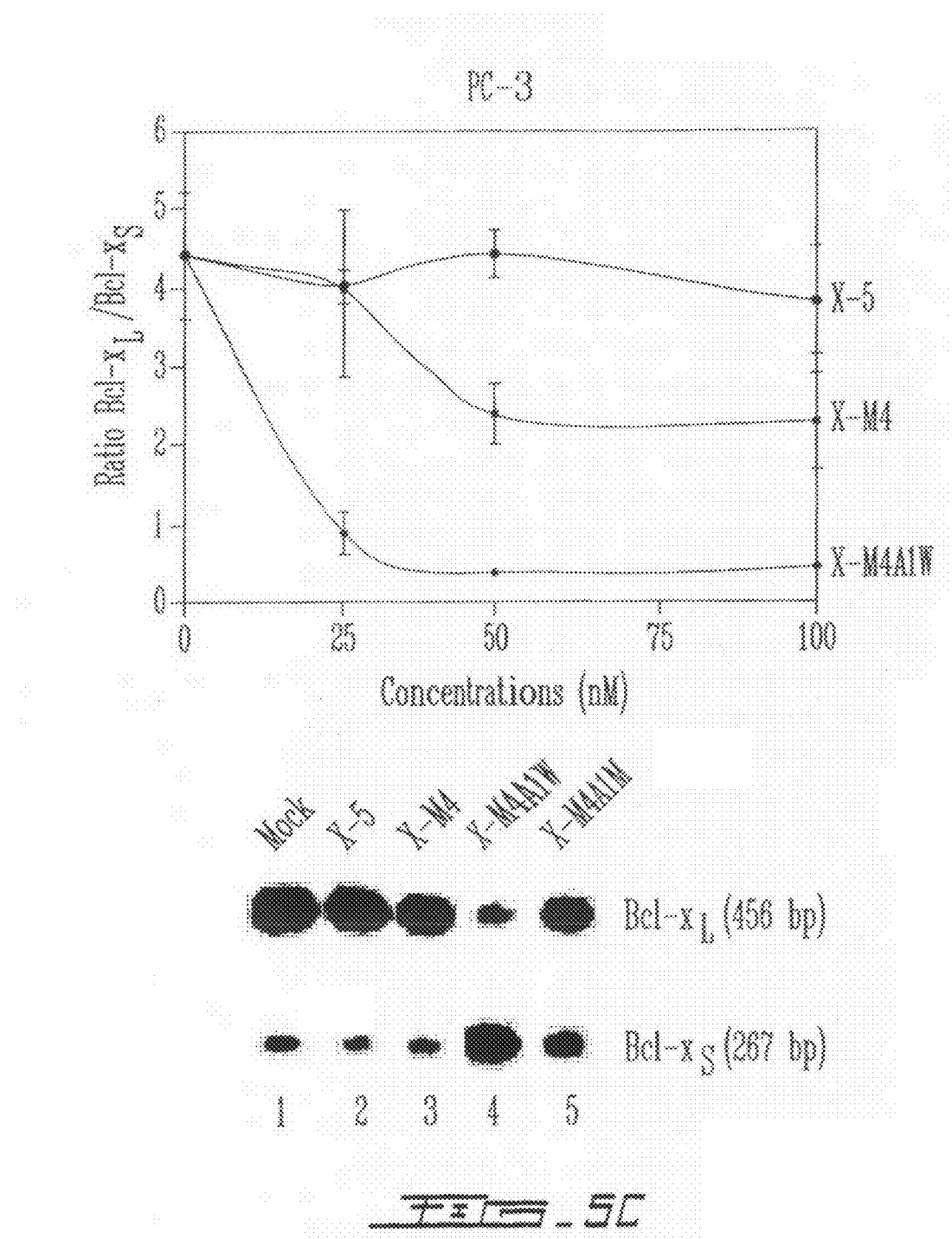

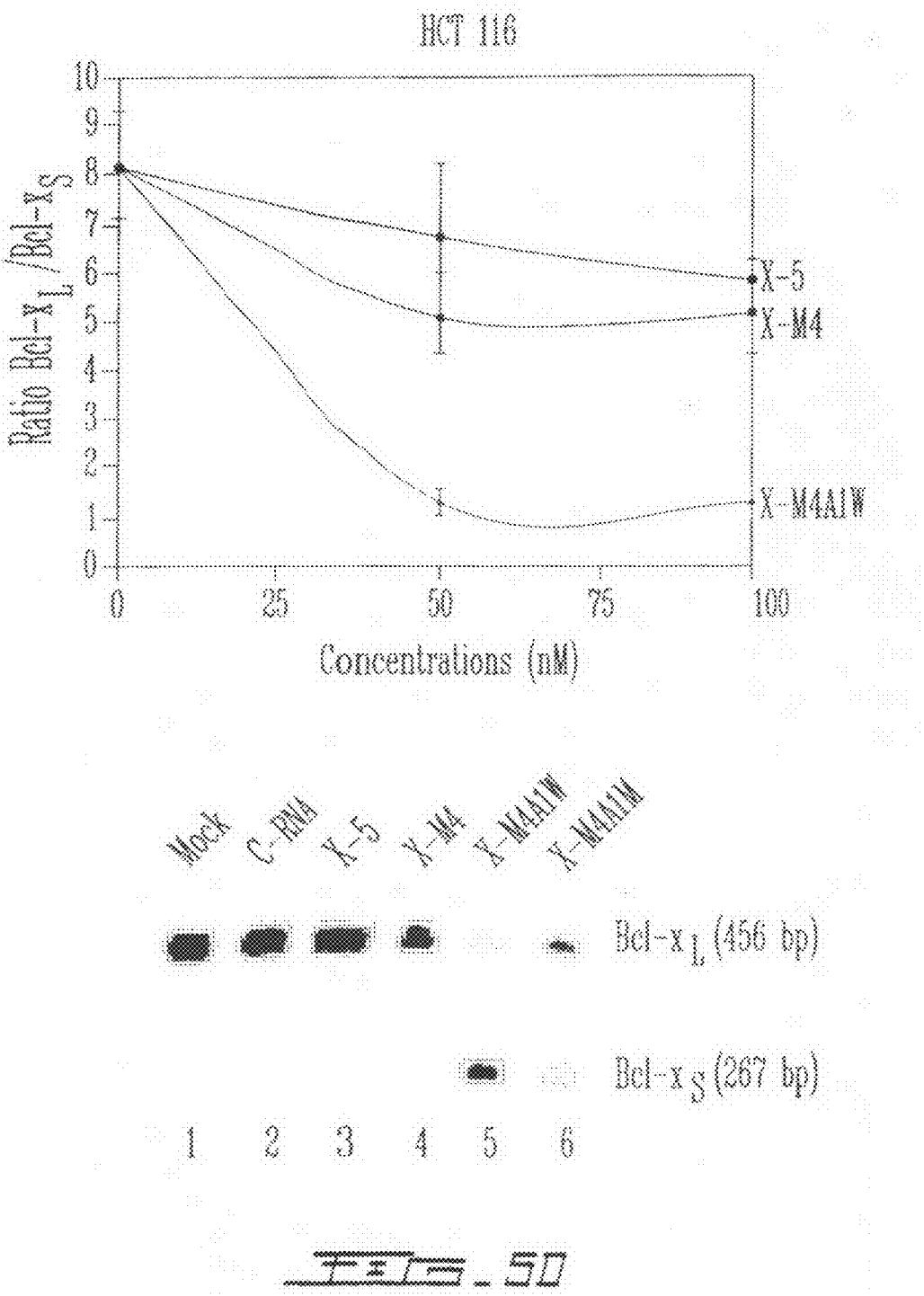

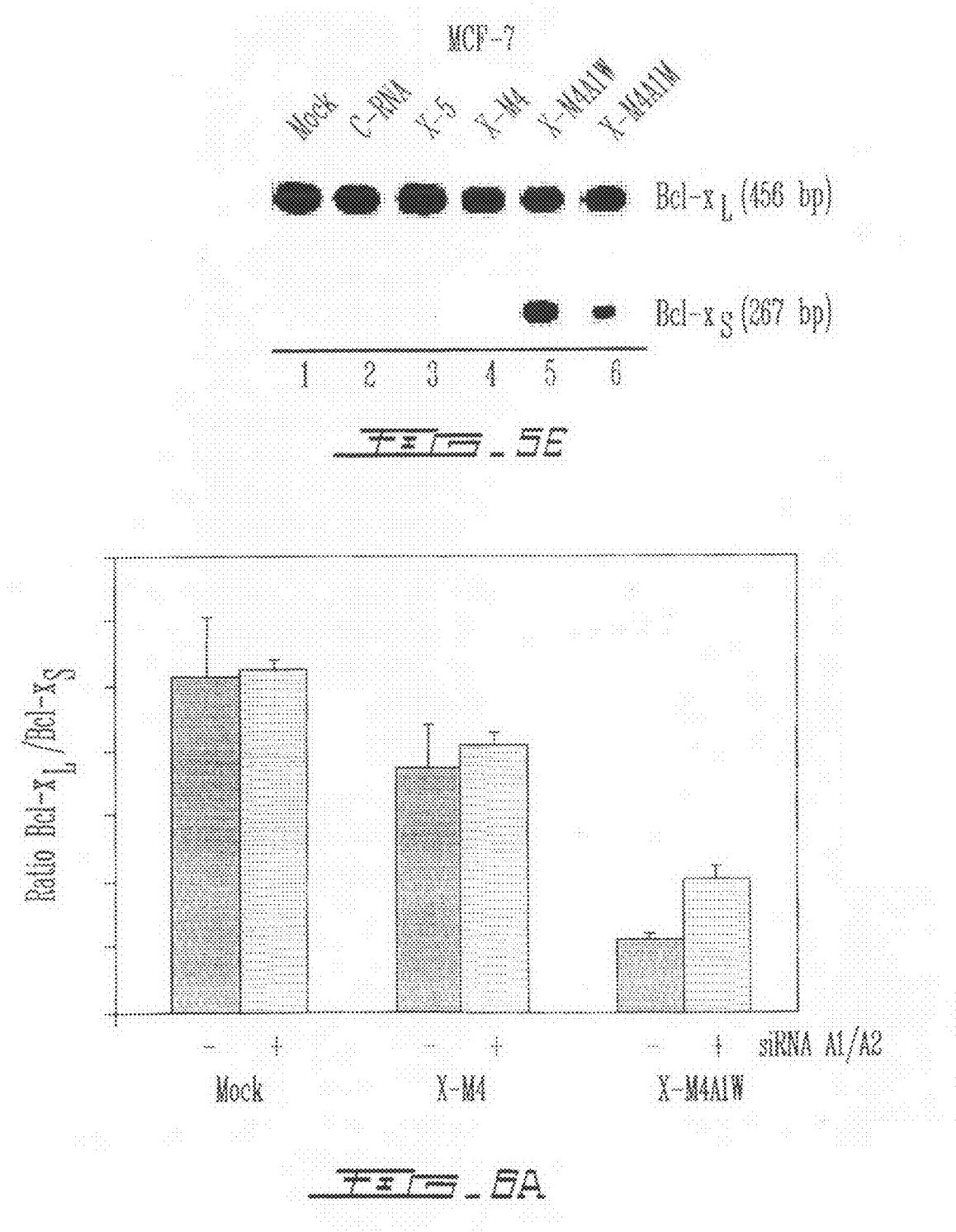

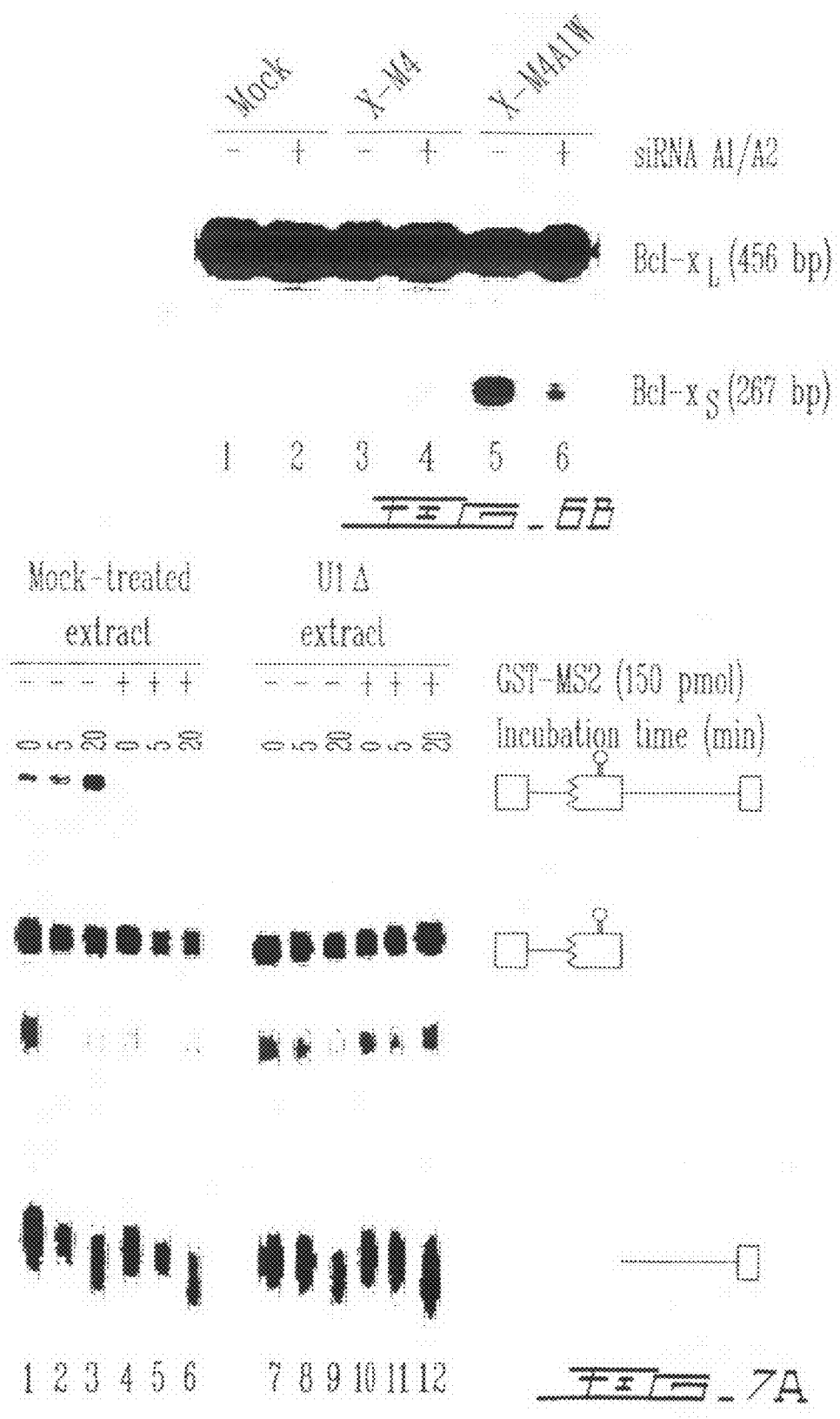

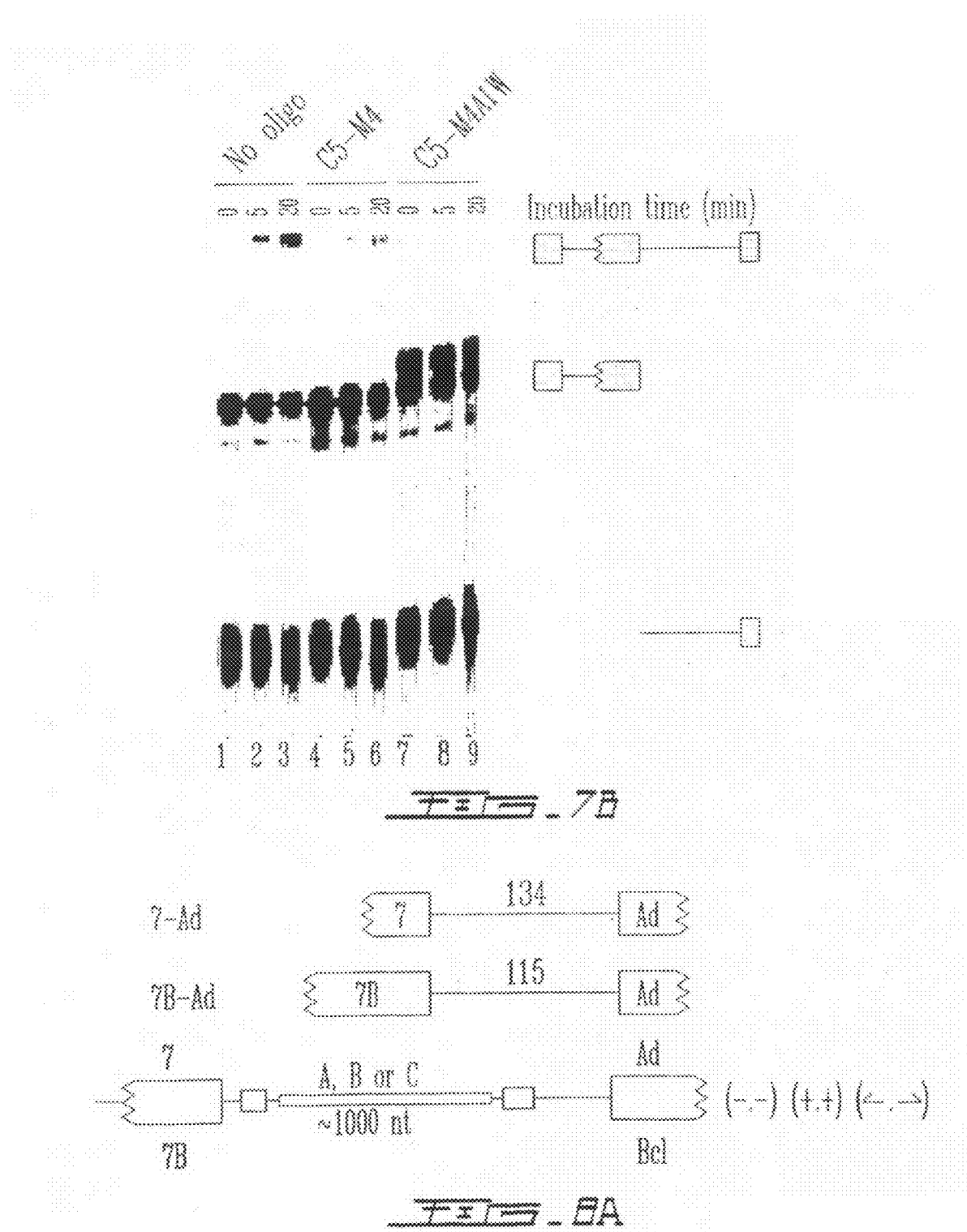

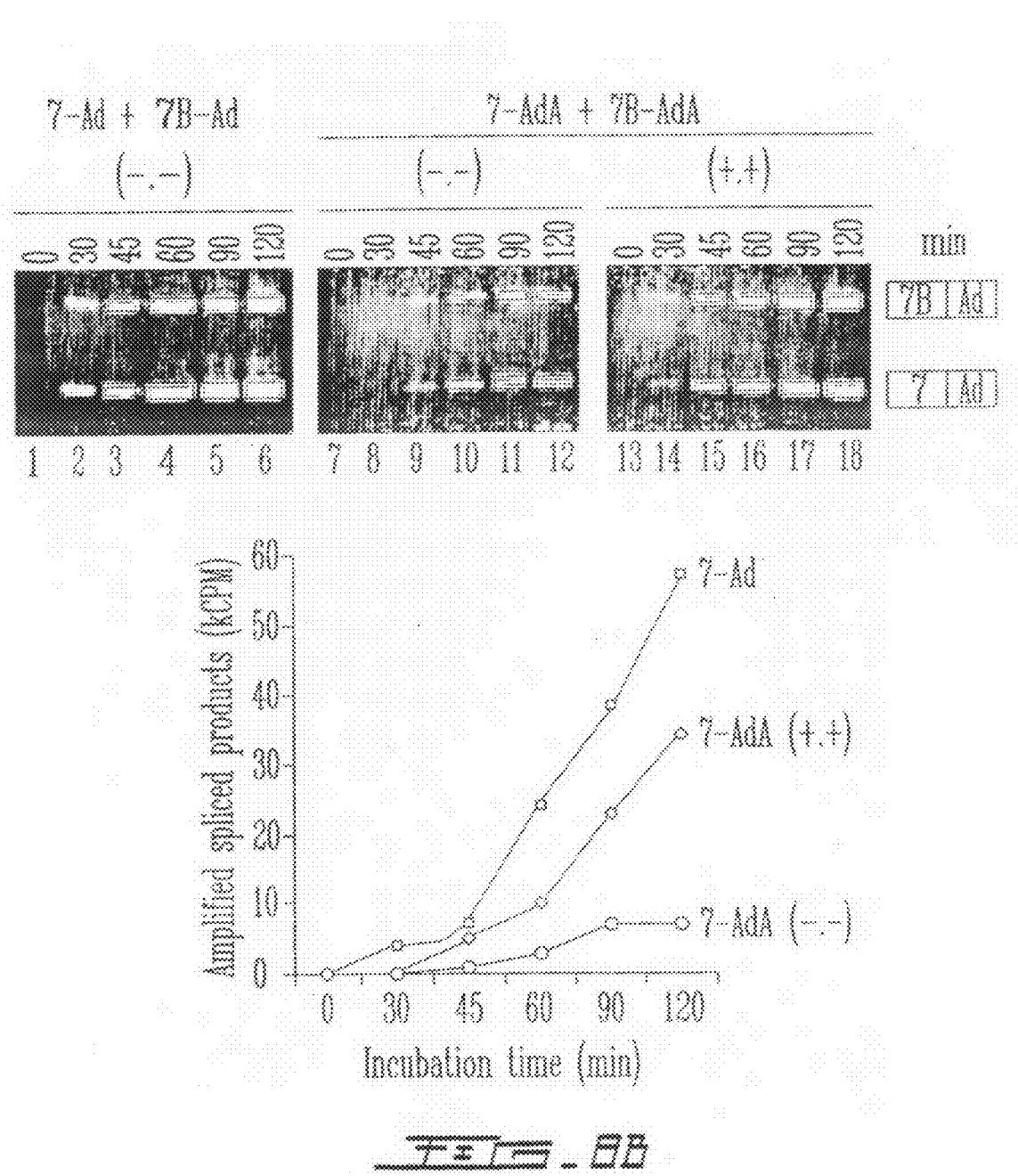

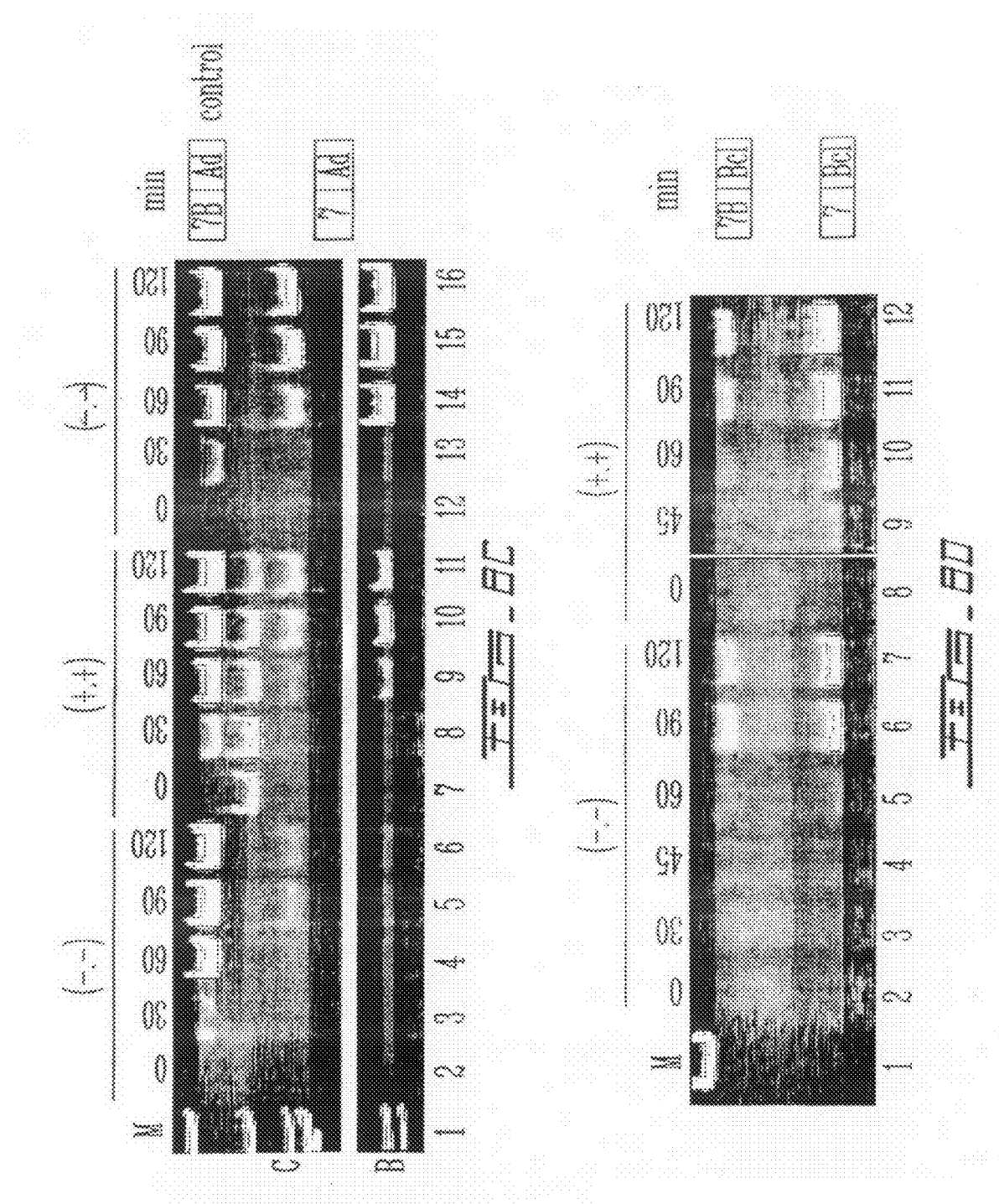

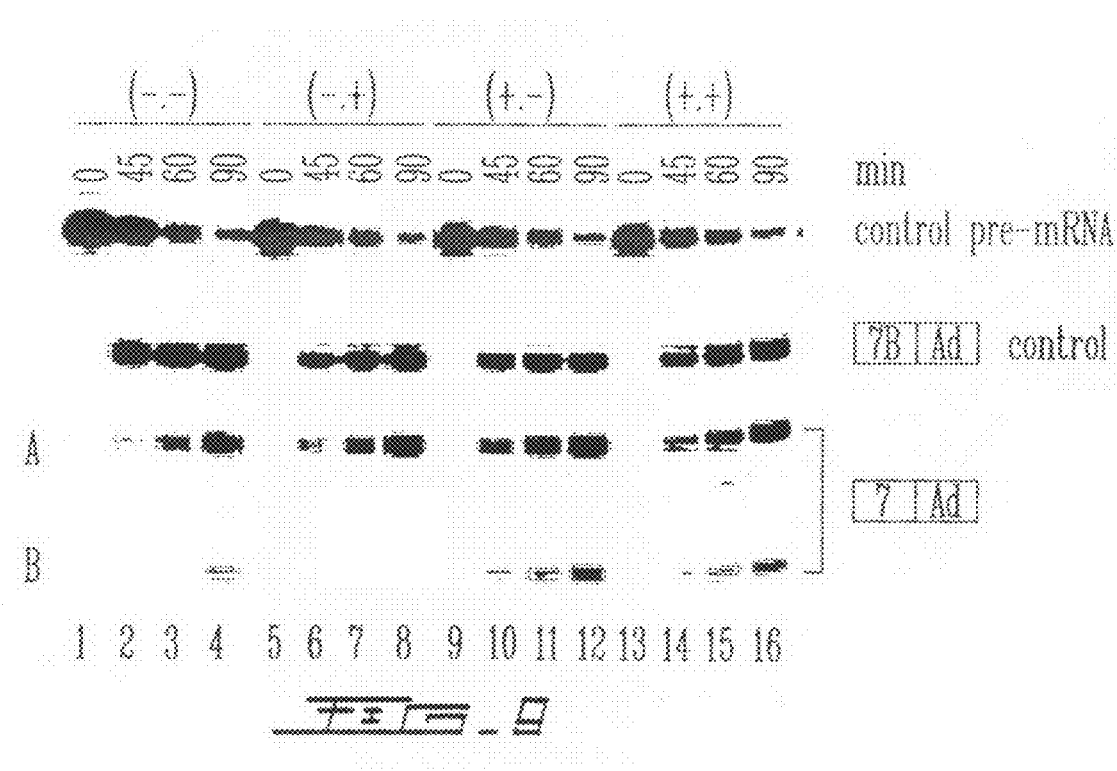

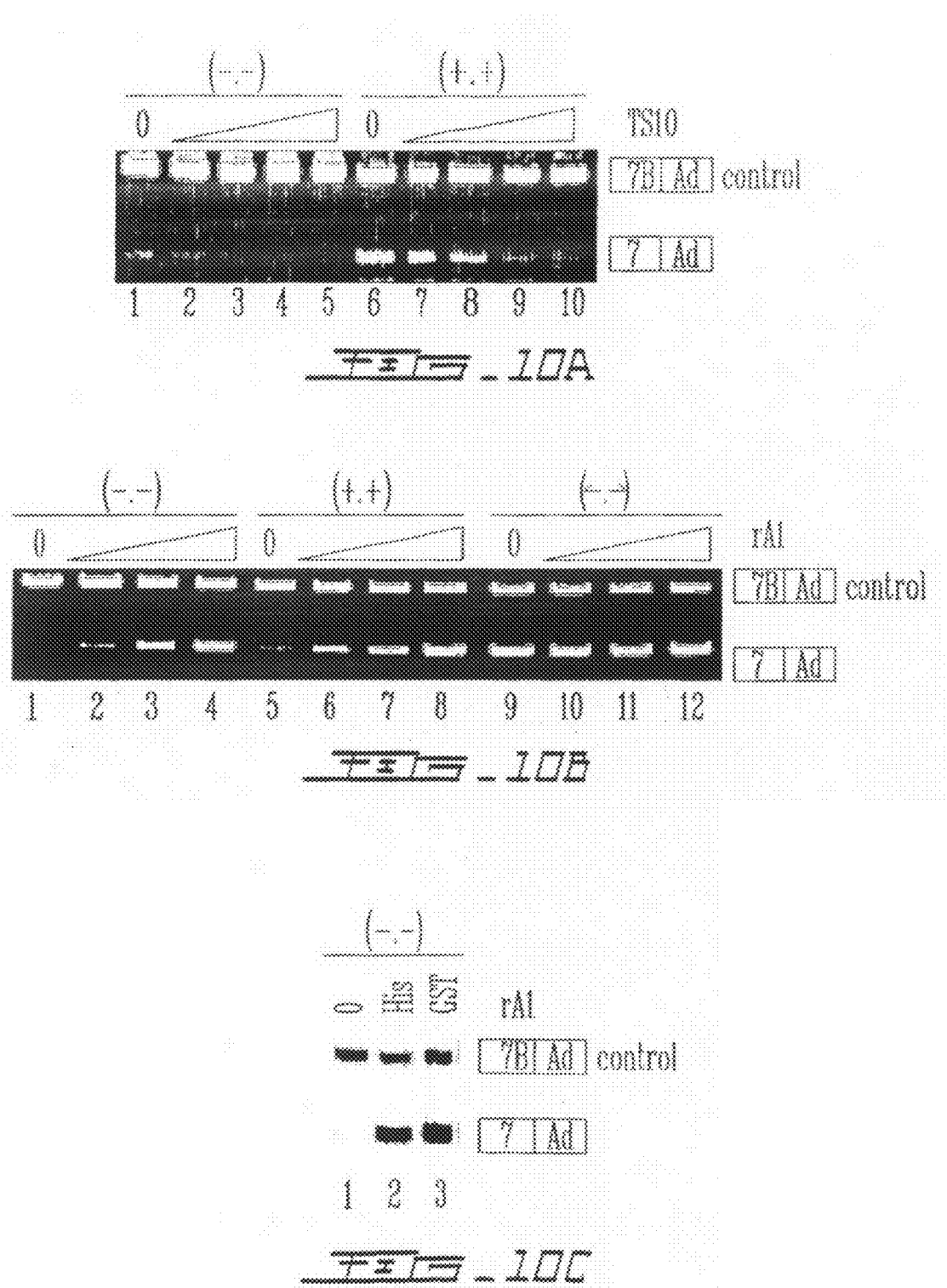

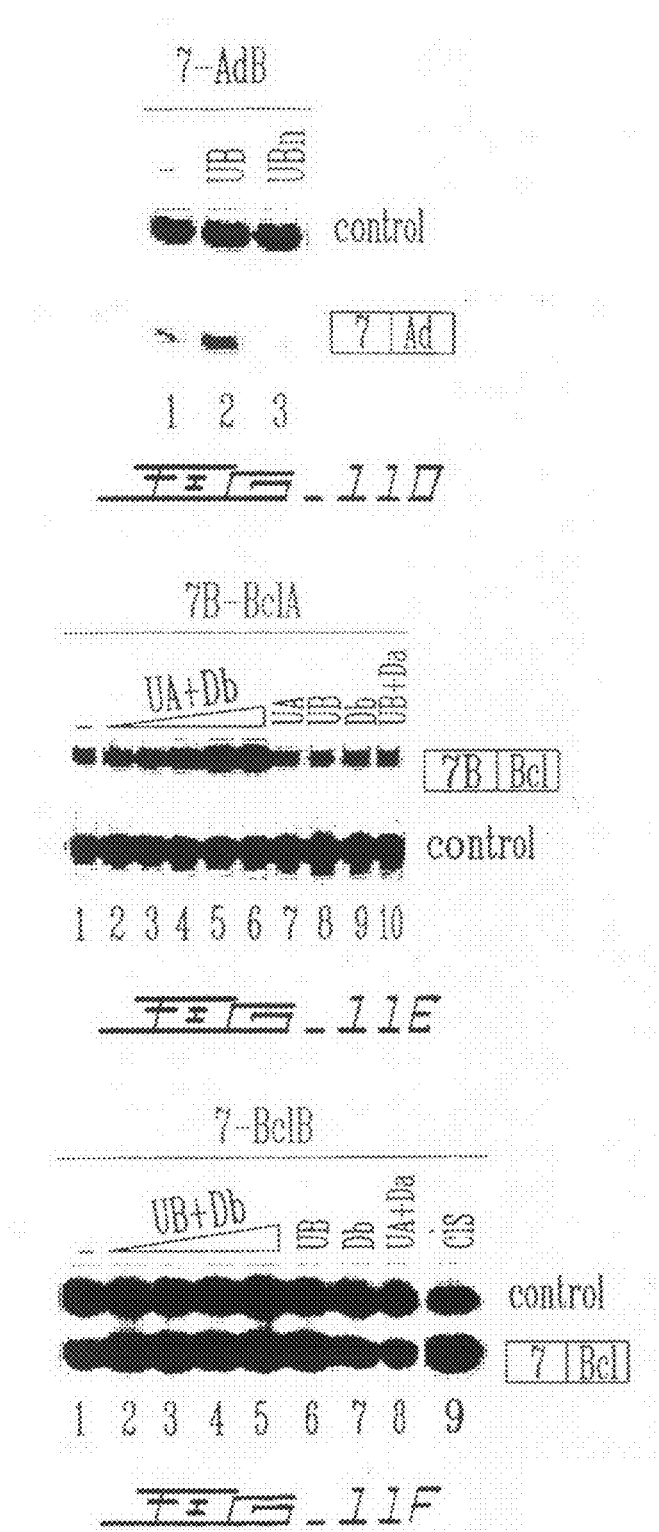

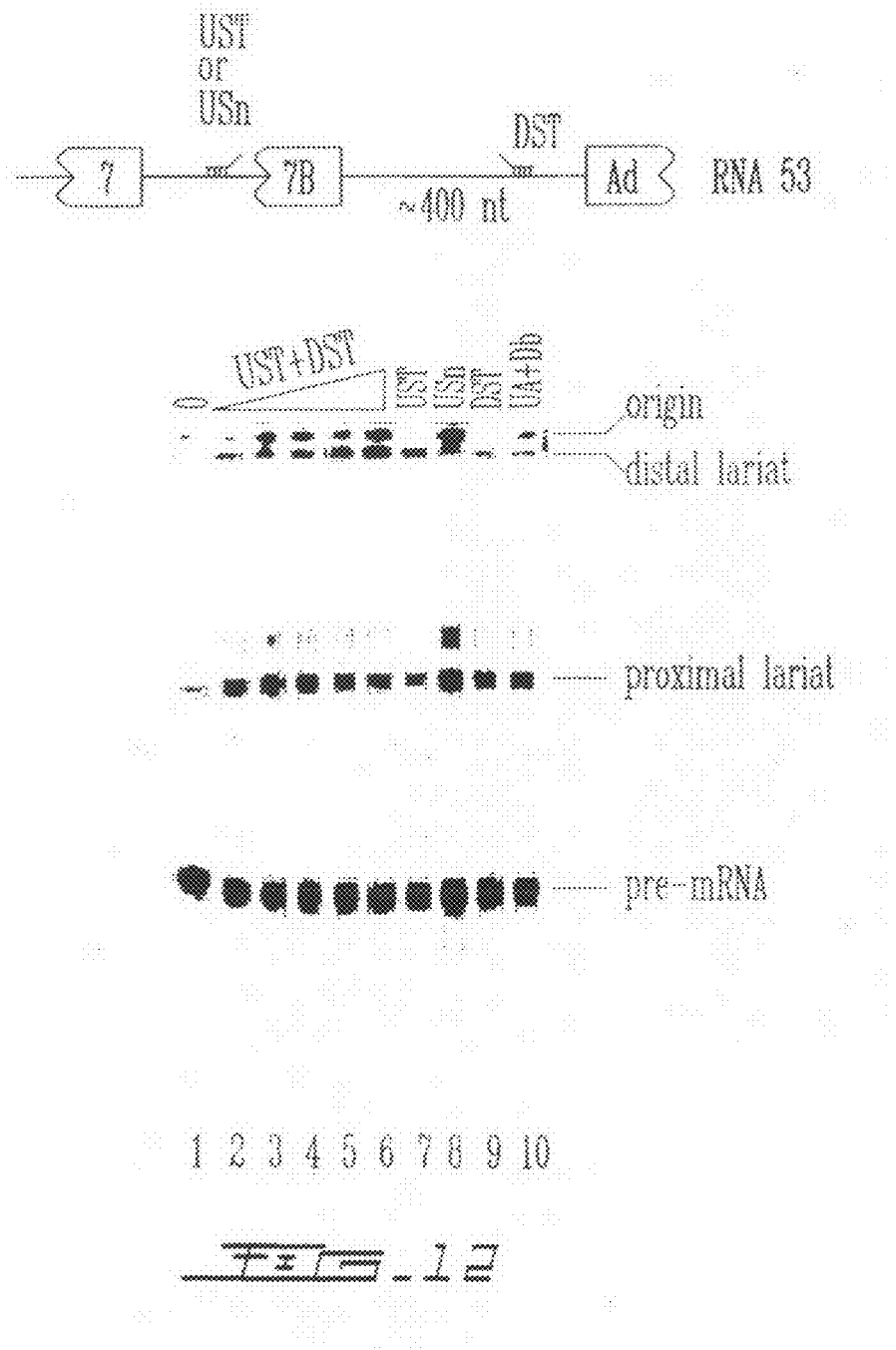

SEQUENCE LISTING

```
<160> NUMBER OF SEQ ID NOS: 33

<210> SEQ ID NO 1
<211> LENGTH: 18
<212> TYPE: DNA
<213> ORGANISM: Artificial Sequence
<220> FEATURE:
<223> OTHER INFORMATION: extension of the oligonucleotide-protein
      conjugate

<400> SEQUENCE: 1
cguacaccau caggguac                                                 18

<210> SEQ ID NO 2
<211> LENGTH: 18
<212> TYPE: DNA
<213> ORGANISM: Artificial Sequence
<220> FEATURE:
<223> OTHER INFORMATION: +7 to -11 proximal 5' splice site

<400> SEQUENCE: 2
uaccuaccac uaccaccg                                                 18

<210> SEQ ID NO 3
<211> LENGTH: 18
<212> TYPE: DNA
<213> ORGANISM: Artificial Sequence
<220> FEATURE:
<223> OTHER INFORMATION: -26 to -43 proximal 5' splice site

<400> SEQUENCE: 3
ccuccuccgu uguuauag                                                 18

<210> SEQ ID NO 4
<211> LENGTH: 20
<212> TYPE: DNA
<213> ORGANISM: Artificial Sequence
<220> FEATURE:
<223> OTHER INFORMATION: -4 to -23 proximal 5' splice site

<400> SEQUENCE: 4
uaccaccgcc aaagccgccu                                               20
```

```
<210> SEQ ID NO 5
<211> LENGTH: 16
<212> TYPE: DNA
<213> ORGANISM: Artificial Sequence
<220> FEATURE:
<223> OTHER INFORMATION: hnRNP A1 binding site of C5-M4A1
      oligonucleotide

<400> SEQUENCE: 5
tttttgatag ggaaat                                                   16

<210> SEQ ID NO 6
<211> LENGTH: 16
<212> TYPE: DNA
<213> ORGANISM: Artificial Sequence
<220> FEATURE:
<223> OTHER INFORMATION: C5-M4CT oligonucleotide

<400> SEQUENCE: 6
gatcacttgt gtcaac                                                   16

<210> SEQ ID NO 7
<211> LENGTH: 20
<212> TYPE: DNA
<213> ORGANISM: Artificial Sequence
<220> FEATURE:
<223> OTHER INFORMATION: hnRNP A1 bonding sites of C5-M4A1W
      oligonucleotide

<400> SEQUENCE: 7
uaugauaggg acuuagggug                                               20

<210> SEQ ID NO 8
<211> LENGTH: 20
<212> TYPE: DNA
<213> ORGANISM: Artificial Sequence
<220> FEATURE:
<223> OTHER INFORMATION: mutated hnRNP A1 binding sites of C5-M4A1M
      oligonucleotide

<400> SEQUENCE: 8
uaugauacgc acuuacgcug                                               20

<210> SEQ ID NO 9
<211> LENGTH: 20
<212> TYPE: DNA
<213> ORGANISM: Artificial Sequence
<220> FEATURE:
<223> OTHER INFORMATION: +7 to -13 proximal 5' splice site

<400> SEQUENCE: 9
uucuuaccca gccgccguuc                                               20

<210> SEQ ID NO 10
<211> LENGTH: 20
<212> TYPE: DNA
<213> ORGANISM: Artificial Sequence
<220> FEATURE:
<223> OTHER INFORMATION: -4 to -23 proximal 5' splice site

<400> SEQUENCE: 10
gccgccguuc uccuggaucc                                               20

<210> SEQ ID NO 11
<211> LENGTH: 16
<212> TYPE: DNA
<213> ORGANISM: Artificial Sequence
```

```
<220> FEATURE:
<223> OTHER INFORMATION: hnRNP A1 binding site of X-M4A1 oligonucleotide

<400> SEQUENCE: 11
tttttgatag ggaaat                                                    16

<210> SEQ ID NO 12
<211> LENGTH: 20
<212> TYPE: DNA
<213> ORGANISM: Artificial Sequence
<220> FEATURE:
<223> OTHER INFORMATION: hnRNP A1 binding sites of X-M4A1W
      oligonucleotide

<400> SEQUENCE: 12
uaugauaggg acuuagggug                                                20

<210> SEQ ID NO 13
<211> LENGTH: 20
<212> TYPE: DNA
<213> ORGANISM: Artificial Sequence
<220> FEATURE:
<223> OTHER INFORMATION: mutated hnRNP A1 binding sites of X-M4A1M
      oligonucleotide

<400> SEQUENCE: 13
uaugauacgc acuuacgcug                                                20

<210> SEQ ID NO 14
<211> LENGTH: 18
<212> TYPE: DNA
<213> ORGANISM: Artificial Sequence
<220> FEATURE:
<223> OTHER INFORMATION: control RNA sequence

<400> SEQUENCE: 14
aaugucugcu acuggaag                                                  18

<210> SEQ ID NO 15
<211> LENGTH: 20
<212> TYPE: DNA
<213> ORGANISM: Artificial Sequence
<220> FEATURE:
<223> OTHER INFORMATION: E-Ad primer

<400> SEQUENCE: 15
gagtttgtcc tcaaccgcga                                                20

<210> SEQ ID NO 16
<211> LENGTH: 20
<212> TYPE: DNA
<213> ORGANISM: Artificial Sequence
<220> FEATURE:
<223> OTHER INFORMATION: BclX3 primer

<400> SEQUENCE: 16
tcggctgctg cattgttccc                                                20

<210> SEQ ID NO 17
<211> LENGTH: 21
<212> TYPE: DNA
<213> ORGANISM: Artificial Sequence
<220> FEATURE:
<223> OTHER INFORMATION: T3-5' primer

<400> SEQUENCE: 17
gggaacaaaa gctgggtacc g                                              21
```

<210> SEQ ID NO 18
<211> LENGTH: 40
<212> TYPE: DNA
<213> ORGANISM: Artificial Sequence
<220> FEATURE:
<223> OTHER INFORMATION: UA oligonucleotide

<400> SEQUENCE: 18
ggguaccuuu agaguaggcc cgcugcguga guauccguga                          40

<210> SEQ ID NO 19
<211> LENGTH: 40
<212> TYPE: DNA
<213> ORGANISM: Artificial Sequence
<220> FEATURE:
<223> OTHER INFORMATION: UB oligonucleotide

<400> SEQUENCE: 19
ggguaccuuu agaguaggcc ucggcuuggu guucuuucag                          40

<210> SEQ ID NO 20
<211> LENGTH: 40
<212> TYPE: DNA
<213> ORGANISM: Artificial Sequence
<220> FEATURE:
<223> OTHER INFORMATION: UOA oligonucleotide

<400> SEQUENCE: 20
cgcugcguga guauccguga ggguaccuuu agaguaggcc                          40

<210> SEQ ID NO 21
<211> LENGTH: 40
<212> TYPE: DNA
<213> ORGANISM: Artificial Sequence
<220> FEATURE:
<223> OTHER INFORMATION: UOB oligonucleotide

<400> SEQUENCE: 21
gcggcuuggu guucuuucag ggguaccuuu agaguaggcc                          40

<210> SEQ ID NO 22
<211> LENGTH: 40
<212> TYPE: DNA
<213> ORGANISM: Artificial Sequence
<220> FEATURE:
<223> OTHER INFORMATION: UB1 oligonucleotide

<400> SEQUENCE: 22
ggguaccuuu agaguaggcc ugauucucgc ugucagaggc                          40

<210> SEQ ID NO 23
<211> LENGTH: 40
<212> TYPE: DNA
<213> ORGANISM: Artificial Sequence
<220> FEATURE:
<223> OTHER INFORMATION: UB2 oligonucleotide

<400> SEQUENCE: 23
gauuccucug cuggccagga ggguaccuuu agaguaggcc                          40

<210> SEQ ID NO 24
<211> LENGTH: 43
<212> TYPE: DNA
<213> ORGANISM: Artificial Sequence
<220> FEATURE:
<223> OTHER INFORMATION: UBn oligonucleotide

```
<400> SEQUENCE: 24
guucgaucuc guaacgaagg cguacggcuu gguguucuuu cag            43

<210> SEQ ID NO 25
<211> LENGTH: 40
<212> TYPE: DNA
<213> ORGANISM: Artificial Sequence
<220> FEATURE:
<223> OTHER INFORMATION: Da oligonucleotide

<400> SEQUENCE: 25
gacgugcagg ucaagcuuga ggguaccuuu agaguaggcc                40

<210> SEQ ID NO 26
<211> LENGTH: 40
<212> TYPE: DNA
<213> ORGANISM: Artificial Sequence
<220> FEATURE:
<223> OTHER INFORMATION: Db oligonucleotide

<400> SEQUENCE: 26
cucugggcca gguaaagggc ggguaccuuu agaguaggcc                40

<210> SEQ ID NO 27
<211> LENGTH: 40
<212> TYPE: DNA
<213> ORGANISM: Artificial Sequence
<220> FEATURE:
<223> OTHER INFORMATION: UST oligonucleotide

<400> SEQUENCE: 27
ggguaccuuu agaguaggcc uccuguccac cagggcugca                40

<210> SEQ ID NO 28
<211> LENGTH: 45
<212> TYPE: DNA
<213> ORGANISM: Artificial Sequence
<220> FEATURE:
<223> OTHER INFORMATION: USn oligonucleotide

<400> SEQUENCE: 28
guucgaucuc guaacgaagg cguagcuguc caccagggcu gcacc          45

<210> SEQ ID NO 29
<211> LENGTH: 40
<212> TYPE: DNA
<213> ORGANISM: Artificial Sequence
<220> FEATURE:
<223> OTHER INFORMATION: DST oligonucleotide

<400> SEQUENCE: 29
ccuucaccca ggcugugccg ggguaccuuu agaguaggcc                40

<210> SEQ ID NO 30
<211> LENGTH: 18
<212> TYPE: DNA
<213> ORGANISM: Artificial Sequence
<220> FEATURE:
<223> OTHER INFORMATION: Oligonucleotide B

<400> SEQUENCE: 30
gatccggccg atatcgcg                                        18
```

```
<210> SEQ ID NO 31
<211> LENGTH: 18
<212> TYPE: DNA
<213> ORGANISM: Artificial Sequence
<220> FEATURE:
<223> OTHER INFORMATION: Oligonucleotide R

<400> SEQUENCE: 31
aattcgcgat atcggccg                                                 18

<210> SEQ ID NO 32
<211> LENGTH: 18
<212> TYPE: DNA
<213> ORGANISM: Artificial Sequence
<220> FEATURE:
<223> OTHER INFORMATION: Oligo A

<400> SEQUENCE: 32
uaccuaccac uaccaccg                                                 18

<210> SEQ ID NO 33
<211> LENGTH: 18
<212> TYPE: DNA
<213> ORGANISM: Artificial Sequence
<220> FEATURE:
<223> OTHER INFORMATION: Oligo B

<400> SEQUENCE: 33
ccuccuccgu uguuauag                                                 18
```

METHODS TO REPROGRAM SPLICE SITE SELECTION IN PRE-MESSENGER RNAS

CROSS REFERENCE TO RELATED APPLICATIONS

The present application is a continuation of U.S. application Ser. No. 10/524,359 filed Aug. 9, 2005 now abandoned, which is a National State Application and claims the priority of co-pending PCT Application No. PCT/CA2003/000988 filed Jun. 30, 2003, which in turn, claims priority from U.S. Provisional Patent Application Serial No. 60/402,765 filed Aug. 12, 2002. Applicants claim the benefits of 35 U.S.C. §120 and/or priority under 35 U.S.C. §119 as to the said United States and the PCT Applications, and the entire disclosures of these applications are incorporated herein by reference in their entireties.

BACKGROUND OF THE INVENTION (a) Field of the Invention

This invention relates to splice site selection, a process required for the generation of mRNAs encoding different proteins.

(b) Description of Prior Art

The completion of genome sequencing efforts for the *Drosophila*, the mouse and the human genomes has led to the conclusion that complex organisms have a smaller than expected set of protein-coding genes. In contrast, the full complement of proteins found in complex animals is much more diverse. While post-translational modifications probably account for a good fraction of protein diversity, the principal mechanism used to generate protein diversification is likely due to alternative pre-mRNA splicing mechanisms which act post-transcriptionally (Maniatis, T. and Tasic, B, (2002) Nature 418:236, Black, D. L., (2003), Annu. Rev. Biochem. 72:291-336).

Recent estimates based on analyses of Expressed Sequences Tags (ESTs) corresponding to mRNAs predict that at least 35% of all human genes are alternatively spliced. Given that ESTs only cover a portion of the mRNA transcript, often corresponding to the non-coding 3' end of the mRNA, this number is likely to be an underestimate. A recent analysis of chromosome 22 estimates the number of genes expressed that are alternatively spliced to be on the order of 59%.

Eukaryotic mRNAs are transcribed as precursors, or pre-mRNAs, which contain intronic sequences. These intronic sequences are excised and the exons are spliced together to form mature mRNA. The basic biochemical reactions involved in splicing are relatively well-known. A transcribed pre-mRNA contains a 5' exon-intron junction, or splice site, which is marked by the consensus sequence CAG/GTAAGT (where/is the exon-intron junction); a 3' splice site marked by the consensus sequence $Y_n$CAG/(Y=Pyrimidines and n=3 to 12); a branchpoint about 25-100 nucleotides upstream of the 3' splice site; and a polypyrimidine track. The splicing event itself requires the binding of several RNA binding proteins and ribonucleoprotein particules (e.g. snRNPs) to form the spliceosome. After spliceosome assembly, two transesterification reactions follow which result in the fusion of the two exon sequences and the release of the lariat-shaped intron.

Given the number of introns and the potential splice sites within a given gene, alternative splicing can produce a variety of mRNA products from one pre-mRNA molecule. The consequences of alternative splicing range from controlling protein expression, by excluding and including stop codons, to allowing for the diversification of protein products. Alternative splicing has an extremely important role in expanding the protein repertoire of any given species by allowing for more transcripts and therefore protein products from a single gene.

While genes that contain a single alternative splicing unit can produce two spliced isoforms, it is not uncommon for genes hosting multiple alternative splicing units to generate ten or more distinct mRNAs. For example, the alternative splicing of troponin T and CD44 pre-mRNAs can generate 64 and more than 2000 isoforms, respectively. The most striking example to date is the splicing of the *Drosophila* gene that codes for DSCAM, a protein involved in axon guidance. Due to 95 different exons distributed in four alternatively spliced regions, a single DSCAM gene has the potential to generate 38,016 different DSCAM proteins, a number which is three times the total number of genes in *Drosophila*. If we assume a conservative average of five isoforms per alternatively spliced gene, the identity of more than 85% of the whole collection of human proteins would be determined by alternative pre-mRNA splicing.

Although alternative pre-mRNA splicing is a powerful contributor to protein diversity in mammals, relatively little is known about the identity of modulating factors and the underlying molecular mechanisms that control splice site selection. Recent progress has identified a variety of non-splice site elements that can positively or negatively affect splice site recognition. In addition, splicing enhancers, RNA binding proteins, and silencer elements have also been shown to play a role in the natural regulation of alternative splicing.

The effect of alternatively including or excluding exons, portions of exons, or introns, can have a broad range of effects on the structure and activity of proteins. In some transcripts, whole functional domains (e.g., DNA binding domain, transcription-activating domain, membrane-anchoring domain, localization domain) can be added or removed by alternative splicing. In other examples, the inclusion of an exon carrying a stop codon can yield a shortened and sometimes inactive protein. In other systems, the introduction of an early stop codon can result in a truncated protein, transforming a membrane bound protein into a soluble protein, for example, or an unstable mRNA. The differential use of splice sites is often regulated in a developmental, cellular, tissue, and sex-specific manner. The functional impact of alternative splicing in a variety of cellular processes including neuronal connectivity, electrical tuning in hair cells, tumor-progression, apoptosis, and signaling events, is just starting to be documented.

Perturbations in alternative splicing have been associated with human genetic diseases and cancer. There are many examples of cancers where an alternatively spliced isoform of a protein has increased ligand affinity or loss of tumor suppressor activity which contributes to neoplastic growth. For example, the inappropriate inclusion of exons in BIN1 mRNA results in the loss of tumor suppressor activity.

Also of particular interest is the contribution of alternative splicing to the control of apoptosis, or programmed cell death. Overexpression of anti-apoptotic proteins (e.g., Bcl-2, Bcl-xL, Bcl-w, Mcl-1) or blocking the expression of pro-apoptotic proteins (e.g., Bax, Bim, Bcl-xS, Bcl-G) protects cells against death stimuli. In contrast, preventing the expression of anti-apoptotic forms promotes or sensitizes cells to death stimuli, a situation also observed by overexpressing pro-apoptotic Bcl-2 family members. Thus, apoptotic pathways are controlled via a delicate balance between pro- and anti-apoptotic activities and alternative splicing is one mechanism used for careful regulation of the cellular response to death signals.

In a number of cancers and cancer cell lines, the ratio of the splice variants is frequently shifted to favor production of the anti-apoptotic form. For example, overexpression of Bcl-xL is associated with decreased apoptosis in tumors, resistance to chemotherapeutic drugs, and poor clinical outcome. Given that many genes are alternatively spliced to produce proteins with opposing effects on apoptosis, perturbations that would shift alternative splicing toward the pro-apoptotic forms may help reverse the malignant phenotype of cancer cells. Thus, the ability to shift splice site selection in favor of pro-apoptotic variants could become a valuable anti-cancer strategy.

Because alternative splicing controls the production and activity of many types of proteins implicated in a variety of pathways, reprogramming splice site selection by preventing the use of one site to the benefit of another competing site would enable the manipulation of protein production and protein function in a general manner. Every aspect of the life of a cell, a tissue or an organism could therefore be affected by methods that block or influence the use of specific splice sites. Alternative splicing has been documented for kinases, transcription factors, trans-membrane protein and receptors, nucleic-acid binding proteins, metabolic enzymes, secreted proteins, extracellular matrix proteins, as well as other proteins. Accordingly, reprogramming the alternative splicing of any of these proteins has the potential to affect the function of each of these proteins.

Given the pivotal role that alternative splicing plays in the diversification of protein function, strategies capable of controlling or reprogramming splice site selection could have an immense impact on our ability to address the function of individual isoforms, as well as providing novel and specific tools to modify or reprogram cellular processes. Approaches that target alternative splicing could therefore provide specific ways to modulate the expression of spliced isoforms with distinct activities. In addition to treating cancer, splicing interference strategies have potential therapeutic values in a wide range of genetic diseases that are caused by point mutations affecting splice site selection. In fact, 15% of all genetic defects (e.g., thalassemia, haemophilia, retinoblastoma, cystic fibrosis, analbuminemia, Lesch-Nyhan syndrome) are caused by splice site mutations.

It is clear that there remains a need for effective methods for controlling or reprogramming splice site selection. Such strategies could have an immense impact on our ability to address the function of individual protein isoforms, as well as providing novel and specific tools to modify or reprogram cellular processes such as apoptosis for the treatment of human disease.

Exons represent approximately 1% of the human genome and range in size from 1 to 1000 nt, with an mean size for internal exons of 145 nt. In contrast, introns constitute 24% of our genome with sizes ranging from 60 to more than 200 000 nt. The mean size of human introns is more than 3, 300 nt and nearly 20% of human introns are longer than 5 Kb. The efficient and accurate removal of introns is crucial for the production of functional mRNAs. For long introns, it is easy to envision the difficulties associated with finding and committing a pair of splice sites when such sites are separated by several thousands of nucleotides. The presence of intronic sequences that resemble splicing signals may also promote a multitude of weaker and non-productive interactions that will decrease the pairing efficiency of correct splice sites. Finally, the long distance separating these splicing partners means that they will be synthesized at different times. Consequently, the 5' splice site must remain available until the authentic 3' splice site has been synthesized. These potential problems may explain why short introns are more prevalent in highly expressed genes. Understanding how the removal of long introns occurs efficiently and accurately remains a tremendous challenge for which very little experimental work has been accomplished. In *Drosophila*, the removal of a 74 kb-long intron in the Ultrabithorax gene has been shown to occur by successive steps, each one regenerating a 5' splice site which is used in the next step until complete intron removal has been carried out. In mammals, intron size can influence alternative splicing (Bell, M.V., et al., (1998), Mol. Cell. Biol. 18:5930-5941) but the mechanisms that enforce the efficient removal of long introns have not yet been investigated.

Some of the decisions associated with the removal of long introns are similar to the choices made by the splicing machinery during the selection of alternative splice sites. Selecting the appropriate pair of splice sites in alternative splicing units requires the contribution of many types of elements that are recognized by different classes of proteins including SR and hnRNP proteins. hnRNP A1 was the first protein of its class being attributed a function in splice site selection based on its ability to antagonize the activity of the SR protein SF2/ASF in a 5' splice site selection assay. A role for the hnRNP A/B proteins in the alternative splicing of many mammalian and viral pre-mRNAs has now been documented (Chabot et al., (2003), Regulation of alternative splicing, Springer-Verlag Gmby & Co., Heidelberg, vol 31, pp. 59-88).

It would be highly desirable to be provided with methods of modulating splice site selection.

SUMMARY OF THE INVENTION

The present invention features a method of modulating splice site selection. It is described herein that using a hybrid oligonucleotide containing a protein binding site and sequences complementary to sequences upstream of a splice site (i.e., in the exon preceding the 5' splice site, for example) allows for a specific inhibition of splicing. By interfering with specific splice site selection, one can therefore control or modify the mRNA and protein products that are generated from any given gene. Given that a large percentage of genes use alternative splice site selection to produce a great number of mRNAs, the utility of this invention is quite extensive both for therapeutic purposes and as a more general tool for research purposes.

In accordance with the present invention, there is provided a method of modulating splice site selection and splicing thereof, the method comprising the step of hybridizing an oligonucleotide-protein conjugate to a target pre-mRNA molecule in a cell or cell extract, wherein the oligonucleotide-protein conjugate comprises an oligonucleotide moiety capable of binding to a protein moiety which comprises at least two distinct sequence elements:

(i) a nucleic acid sequence that is complementary to a specific region upstream of the splice site in the target pre-mRNA molecule; and (ii) an extension containing a protein binding site sequence element for covalently binding a protein; and wherein the protein moiety comprises a protein capable of modulating splicing of the splice site upon binding with the protein binding site.

In a preferred embodiment of the present invention, the binding of the protein is effected prior to hybridizing of the oligonucleotide moiety to the target pre-mRNA molecule or thereafter.

The modulating activity is one of increasing or repressing splice site selection and splicing thereof.

In a preferred embodiment of the present invention, the cell is in a patient and in a more preferred embodiment of the present invention, the patient is a mammalian.

In a preferred embodiment of the present invention, the nucleic acid sequence element is at least 70%, preferably 85%, more preferably 90%, and most preferably 95% complementary to at least 8 nucleotides found upstream of the splice site, more preferably substantially complementary to at least eight nucleotides beginning 16 to 36 base pairs upstream of the splice site and most preferably substantially complementary to at least eight nucleotides beginning 20 to 26 base pairs upstream of the splice site.

In one embodiment of the present invention, the protein is, one that binds to a single-stranded or double stranded nucleic acid molecule.

In a preferred embodiment of the present invention, the protein is selected from the group consisting of SR proteins, hnRNP proteins, RNA binding proteins, ribonucleoprotein, nucleic acid binding-protein and single stranded DNA binding proteins. The hnRNP protein is preferentially hnRNP A1/A2 protein.

In accordance with the present invention, there is provided an oligonucleotide-protein conjugate for modulating splice site selection and splicing thereof in a target pre-mRNA molecule present in a cell or cell extract, which comprises an oligonucleotide moiety covalently attached to a protein moiety, wherein the oligonucleotide moiety comprises at least two distinct sequence elements:

(i) a nucleic acid sequence that is complementary to a specific region upstream of the splice site in the target pre-mRNA molecule; and (ii) an extension containing a protein binding site sequence element, wherein the hybridizing of the oligonucleotide modulates splicing of the splice site in the target pre-mRNA molecule; and wherein the protein moiety comprises a protein capable of modulating splicing of the splice site.

In a preferred embodiment of the present invention, the oligonucleotide-protein conjugate is having an extension of the sequence

```
5' CGU ACA CCA UCA GGG UAC-3'.    (SEQ ID NO: 1)
```

In another embodiment of the present invention, the oligonucleotide-protein conjugate is having an oligonucleotide moiety comprising a sequence selected from the group consisting of SEQ ID NO:1, SEQ ID NO:2 to SEQ ID NO:14 and SEQ ID NO:18 to SEQ ID NO:33.

In accordance with the present invention, there is provided a method of creating an alternate form of mRNA comprising the step of administering to a cell or a cell extract a sufficient amount of the oligonucleotide-protein conjugate of the present invention.

In accordance with the present invention, there is provided a method of creating an alternate form of a protein comprising the step of administering to a cell or a cell extract a sufficient amount of the oligonucleotide-protein conjugate of the present invention In a preferred embodiment of the present invention, the alternate form of a protein functions as a dominant negative.

In accordance with the present invention, there is provided a method of reducing and/or inhibiting expression of an mRNA molecule or protein, the method comprising the step of administering to a cell or a cell extract a sufficient amount of the oligonucleotide-protein conjugate of the present invention.

In accordance with the present invention, there is provided a method of reducing and/or inhibiting neuronal differentiation, the method comprising the step of administering to a cell or a cell extract a sufficient amount of the oligonucleotide-protein conjugate of the present invention.

In accordance with the present invention, there is provided a method of preventing a viral infection in a patient, the method comprising the step of administering a therapeutically effective amount of the oligonucleotide-protein conjugate of the present invention to the patient.

In a preferred embodiment of the present invention, the viral infection is caused by human immunodeficiency virus.

In accordance with the present invention, there is provided a method for treating a disease resulting from a mutation leading to aberrant splicing in a patient, the method comprising the step of administering a therapeutically effective amount of the oligonucleotide-protein conjugate of the present invention to the patient.

In a preferred embodiment of the present invention, the disease is selected from the group consisting of β-thalassemia, cystic fibrosis, haemophilia, retinoblastoma, analbuminemia, Lesch-Nyhan syndrome, acute intermittent porphyria, breast and ovarian cancer, carbohydrate-deficient glycoprotein syndrome type 1a, cerbrotendinous xanthomatosis, Ehlers-Danlos syndrome type VI, Fanconi anemia, frontotemporal dementia, HPRT deficiency, Leigh's encephalomyelopathy, Marfan syndrome, metachromatic leukodystrophy juvenile form), neurofibromatosis type 1, OCT deficiency, porphyria cutanea tarda, Sandhoff disease, severe combined immunodeficiency, spinal muscle atrophy, tyrosinemia type 1, and Duchenne muscular dystrophy.

In accordance with the present invention, there is provided a method for promoting cell death in a patient, the method comprising the step of administering an effective amount of the oligonucleotide-protein conjugate of the present invention to the patient.

In accordance with the present invention, there is provided a method for preventing and/or reducing the growth of tumor cells in a patient, the method comprising the step of administering a therapeutically effective amount of the oligonucleotide-protein conjugate of the present invention to the patient.

In a preferred embodiment of the present invention, the tumor cells are selected from the group consisting of lung cancer cells, liver cancer cells, pancreatic cancer cells, brain cancer cells, colon cancer cells, kidney cancer cells, bone cancer cells, breast cancer cells, prostate cancer cells, uterine cancer cells, lymphoma cells, melanoma cells, myeloma cells, adenocarcinoma cells, thymoma cells and plasmacytoma cells.

It is also provided in the present application the oligonucleotide moiety for modulating splice site selection and splicing thereof in a target pre-mRNA molecule present in a cell or cell extract, which comprises at least two distinct sequence elements:

(i) a nucleic acid sequence that is complementary to a specific region upstream of the splice site in the target pre-mRNA molecule; and (ii) an extension containing a protein binding site sequence element for covalently binding a protein.

It is also comprised in the present application any of the method previously described using the oligonucleotide moiety of the present invention, where the method also comprises the administrating to the cell or cell extract of a purified protein capable of binding to the protein binding site.

In a preferred embodiment of the present invention, the administration of the oligonucleotide-protein conjugate is effected through a route selected from the group consisting of oral, parenteral, subcutaneous, intradermal, intramuscular, intravenous, intraarterial, topical and nasal route.

In a preferred embodiment of the present invention, the oligonucleotide-protein conjugate is administered in a range varying from 0.001 to 50 mg/kg, more preferably varying from 0.01 to 10 mg/kg, most preferably varying from 0.1 to 5 mg/kg.

The oligonucleotide as used in the present invention is preferably one selected from the table below:

TABLE 1

Oligonucleotides used in the present invention

| Oligonucleotide | Target | Binding site sequence | Complementary region sequence |
|---|---|---|---|
| C5-5' | C5' -/- | | UACCUACCACUACCACCG (SEQ ID NO: 2) +7 to -11 proximal 5' splice site |
| C5-M26 | C5' -/- | | CCUCCUCCGUUGUUAUAG (SEQ ID NO: 3) -26 to -43 proximal 5' splice site |
| C5-M4 | C5' -/- | | UACCACCGCCAAAGCCGCCU (SEQ ID NO: 4) -4 to -23 proximal 5' splice site |
| C5-M4A1 | C5' -/- | TTTTTGA<u>TAGGG</u>AAAT (SEQ ID NO: 5) hnRNP A1 binding site | UACCACCGCCAAAGCCGCCU (SEQ ID NO: 4) -4 to -23 proximal 5' splice site |
| C5-M4CT | C5' -/- | GATCACTTGTGTCAAC (SEQ ID NO: 6) No binding site | UACCACCGCCAAAGCCGCCU (SEQ ID NO: 4) -4 to -23 proximal 5' splice site |
| C5-M4A1W | C5' -/- | UAUGAU<u>AGGGA</u>CUU<u>AGG</u><u>G</u>UG (SEQ ID NO: 7) hnRNP A1 binding site | UACCACCGCCAAAGCCGCCU (SEQ ID NO: 4) -4 to -23 proximal 5' splice site |
| C5-M4A1M | C5' -/- | UAUGAUACGCACUUACGCUG (SEQ ID NO: 8) mutated hnRNP A1 binding sites | UACCACCGCCAAAGCCGCCU (SEQ ID NO: 4) -4 to -23 proximal 5' splice site |
| X-5 | Bcl-x | | UUCUUACCCAGCCGCCGUUC (SEQ ID NO: 9) +7 to -13 proximal 5' splice site |
| X-M4 | Bcl-x | | GCCGCCGUUCUCCUGGAUC C (SEQ ID NO: 10) -4 to -23 proximal 5' splice site |
| X-M4A1 | Bcl-x | TTTTTGA<u>TAGGG</u>AAAT (SEQ ID NO: 11) hnRNP A1 binding site | GCCGCCGUUGUCCUGGAUC C (SEQ ID NO: 10) -4 to -23 proximal 5' splice site |
| X-M4A1W | Bcl-x | UAUGAU<u>AGGGA</u>CUU<u>AGG</u><u>G</u>UG (SEQ ID NO: 12) hnRNP A1 binding site | GCCGCCGUUCUCCUGGAUC C (SEQ ID NO: 10) -4 to -23 proximal 5' splice site |
| X-M4A1M | Bcl-x | UAUGAUACGCACUUACGCUG (SEQ ID NO: 13) mutated hnRNP A1 binding sites | GCCGCCGUUCUCCUGGAUC C (SEQ ID NO: 10) -4 to -23 proximal 5' splice site |
| C-RNA | | AAUGUCUGCUACUGGAAG (SEQ ID NO: 14) | control RNA sequence |

While the first aspect of the invention makes use of hybrid oligo that interferes with splice site recognition because the hybrid: oligo hybridizes close to the splice site, the second aspect of the invention features a method to alter splice site use by using hybrid oligos hybridizing at a greater distance from the splice sites. In this second aspect, we are using hybrid oligos that are bound by hnRNP A1/A2 proteins to influence alternative splicing and the splicing of long introns by a mechanism that involves looping out the sequences between the sites bound by the oligos. Providing A1/A2 through the use of hybrid oligos can therefore position A1/A2 to act on the splicing of large introns and on alternative splicing.

In an alternative embodiment of the present invention, the extension is attached to an other oligo or a secondary structure of the oligonucleotide, to form a binding site for a protein which bound to double-stranded RNA.

For the purpose of the present invention, the following abbreviations and terms are defined below.

The term "3' splice site" is intended to mean pre-mRNA sequences at the 3' intron/exon boundary which generally contains the sequence YnCAG/(where / is the intron exon boundary, Y=pyrimidines and n=3 to 12). The splicing machinery can recognize and bind to the 3' splice site sequences.

The term "5' splice site" is intended to mean pre-mRNA sequences at the 5' exon/intron boundary which generally contains the sequence CAG/GTAAGT (where / is the exon/ intron boundary). The splicing machinery can recognize and bind to the 5' splice site sequences.

The term "alternate form of mRNA" is intended to mean any form of mRNA that is produced through the use of any splice, site other that the dominant splice sites. Non-limiting examples include alternate forms of mRNA produced through the use of cryptic 3' or 5' splice sites, exon skipping, shifting of 5' or 3' splice sites to make exons longer or shorter, and the use of intronic sequences as an exon.

The term "alternative splicing" is intended to mean the use of distinct 5' or 3' splice sites, introns, or exons within a single pre-mRNA to generate multiple RNA and protein isoforms from a single gene. For example, alternative splicing can take the form of one or more skipped exons, variable position of intron splicing, or intron retention.

The term "complementary" is intended to mean the relationship of the nucleotides/bases on two different strands of DNA or RNA, where the bases are paired (guanine with cytidine, adenine with thymine (DNA) or uracil (RNA)). Specifically, the complementarity of the sequences should be sufficient to enable the oligonucleotide to recognize the specified pre-mRNA sequence and to direct binding of the oligonucleotide to the specified pre-mRNA. The region of the oligonucleotide can exhibit at least 70%, preferably 85%, more preferably 90%, and most preferably 95% sequence complementarity to the pre-mRNA being targeted.

The term "cryptic splice site" is intended to mean a normally dormant 5' or 3' splice site which is activated by a mutation or otherwise and can serve as a splicing element. For example, a mutation may activate a 5' splice site which is downstream of the native or dominant 5' splice site. Use of this "cryptic" splice site results in the production of distinct mRNA splicing products that are not produced by the use of the native or dominant splice site.

The term "dominant negative" is intended to mean any distinct isoform of a protein that can inhibit the function of the natural or endogenous form of the protein.

The term "expression" is intended to mean the detection of a gene product or protein product by standard art known methods. For example, protein expression is often detected by western blotting and RNA expression is detected by northern blotting or by RNAse protection assays. To "reduce or inhibit expression" means a decrease of 20% or greater, preferably 30% or greater, more preferably 40% or greater, and most preferably 50% or greater in the level of mRNA or protein detected by the above assays.

The term "hnRNP" is intended to mean any protein belonging to the family of heterogeneous nuclear ribonucleoprotein particles. hnRNP proteins are associated with pre-mRNAs in the nucleus and appear to influence pre-mRNA processing and other aspects of mRNA metabolism and transport. There are over 20 such hnRNP proteins in human cells.

The term "oligonucleotide" is intended to mean polymers, such as DNA and RNA, of nucleotide monomers or nucleic acid analogs thereof, including double and single stranded deoxyribonucleotides, ribonucleotides, α-anomeric forms thereof, and the like. Usually the monomers are linked by phosphodiester linkages, where the term "phosphodiester linkate" refers to phosphodiester bonds or bonds including phosphate analogs thereof, including associated counterions, e.g., H+, NH4+, Na+. The oligonucleotide can also contain a modified backbone such as a morpholino backbone or a peptide nucleic acid (PNA) backbone wherein the deoxyribose phosphate skeleton has been replaced by peptide oligomers. Oligonucleotides typically range in size from a few monomeric units, e.g., 5-40, to several hundreds of monomeric units. Whenever an oligonucleotide is represented by a sequence of letters, such as "ATGCCTG," it will be understood that the nucleotides are in 5' to 3' order from left to right and that "A" denotes adenosine, "C" denotes cytidine, "G" denotes guanosine, "T" denotes thymidine, and "U" denotes uracil, unless otherwise noted. As used herein, it includes the physiologically and pharmaceutically acceptable salts thereof: i.e., salts that retain the desired biological activity of the parent compound and do not impart undesired toxicological effects thereto. Examples of such salts are (a) salts formed with cations such as sodium, potassium, NH4+, magnesium, calcium, polyamines such as spermine and spermidine; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The term "pharmaceutically acceptable carrier" is intended to mean a carrier that is physiologically acceptable to the treated mammal while retaining the therapeutic properties of the compound with which it is administered. One exemplary pharmaceutically acceptable carrier substance is physiological saline. Other physiologically acceptable carriers and their formulations are known to one skilled in the art and described, for example, in Remingtonis Pharmaceutical Sciences, (20th edition), ed. A. Gennaro, 2000, Lippincott, Williams & Wilkins, Philadelphia, Pa.

The term "protein binding site sequence element" is intended to mean a nucleic acid sequence element that contains a binding site for a protein that can interact with single-stranded or double-stranded nucleic acid molecules. The protein binding site sequence element can also include any RNA sequences that are substantially identical to known small RNAs that interact with one or more proteins to form a large RNA/protein complex known as an RNP. Examples of such small RNAs include snRNA, snoRNA, or any other small RNA sequences (e.g. tRNA, 5S RNA, the RNA subunit of telomerase).

The term "small RNA" is intended to mean any short RNA that is not directly involved in protein synthesis. In general small RNAs range in size from 50 to 500 nucleotides, although some can be as long as a thousand base pairs. Small RNAs are metabolically stable and can associate with RNA binding proteins.

The term "snRNA" is intended to mean small nuclear RNA. snRNAs are generally involved in RNA processing. Examples of snRNAs include U1, U2, U4, U5, and U6, which associate with proteins to form small nuclear ribonucleoproteins (snRNPs).

The term "snoRNA" is intended to mean a small nucleolar RNA. SnoRNAs can range in size from 60 to 300 nucleotides, are metabolically stable, and associate with a set of proteins to form small nucleolar ribonucleoproteins (snoRNPs). SnoRNAs generally play a role in RNA synthesis and processing. There are several hundred different snoRNAs which generally fall into two major classes: the box C(RUGAUGA) and D (CUGA) motifs, and the box H (ANANNA) motif and ACA elements. Examples of box C/D snoRNAs include U3, U8, U14, and U22 snoRNA. Examples of box H/ACA RNAs include snR30 and the RNA subunit of telomerase.

The term "splice site selection" is intended to mean the determination by a cell to use one of several potential 5' or 3' splice sites in a pre-mRNA molecule.

The term "SR proteins" is intended to mean any of a family of proteins critical to splicing known as the serine-arginine (SR) family of splicing factors. These proteins function as bridges between the mRNA and several other protein factors.

The term "substantially identical" is intended to mean a nucleic acid exhibiting at least 50%, preferably 85%, more preferably 90%, and most preferably 95% identity to a reference nucleic acid sequence. The length of comparison sequences will generally be at least 8-100 nucleotides, more preferably 10-50 nucleotides, and most preferably 10-25 nucleotides.

Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications.

Formulations of the present invention comprise the oligonucleotide in a physiologically or pharmaceutically acceptable carrier, such as an aqueous carrier. Thus, formulations for use in the present invention include, but are not limited to, those suitable for oral administration, parenteral administration, including subcutaneous, intradermal, intramuscular, intravenous and intraarterial administration, as well as topical administration (i.e., administration of an aerosolized formulation of respirable particles to the lungs of a patient afflicted with cystic fibrosis). The formulations may be conveniently presented in unit dosage form and may be prepared by any of the methods well known in the art. The most suitable route of administration in any given case may depend upon the subject, the nature and severity of the condition being treated, and the particular active compound which is being used.

Other features and advantages of the invention will be apparent from the following description of the preferred embodiments thereof, and from the claims.

All references herein are hereby incorporated by reference.

BRIEF DESCRIPTION OF THE DRAWINGS

FIG. 1 illustrates the effects of oligonucleotide versus protein binding on splice site utilization. Oligonucleotide or purified GST-MS2 protein was added to an in vitro splicing assay and proximal versus distal splice site utilization was determined. For the samples containing purified protein, a model pre-mRNA containing a binding site for MS2 in the vicinity of the proximal 5' splice site was incubated in the HeLa cell extract in the presence or absence of GST-MS2 and splicing was assayed as described above;

FIGS. 2A-C illustrate splicing interference by GST-MS2 protein binding near a 5' splice site. (A) C5' –/– is a model pre-mRNA substrate containing the competing 5' splice sites of mouse hnRNP A1 exon 7 and exon 7B. The C5' –/– pre-mRNA is spliced predominantly to the internal (proximal) 5' splice site of exon 7B. We constructed derivatives carrying the stem-loop binding site for the MS2 bacteriophage coat protein at various positions upstream or downstream of the proximal 5' splice junction (–46, –37, –26, –17, +15, +23 and +31). Another set of derivatives contained the complementary sequence of the MS2 binding sites inserted at the same position (AS derivatives). We also constructed a derivative containing a mutated version of the MS2 binding sites (C5-M26SΔ). (B) Labeled pre-mRNAs were incubated in a HeLa nuclear extract for 2 hours at 30° C. in the presence or the absence of GST-MS2 protein. The extracted RNA was fractionated on a 11% acrylamide denaturing gel. The position of the pre-mRNA and splicing intermediates and products is indicated. (C) Compilation of the effect of positioning of the GST-MS2 protein near a 5'splice site on splice site selection. The level of distal over proximal splicing was compiled for each transcript and the difference between the presence or the absence of GST-MS2 was calculated and plotted in the histogram;

FIGS. 3A-B illustrate splicing interference by GST-MS2 in human 293 cells. (A) The human β-globin mini-gene (DUP5.1) was modified by inserting the MS2 binding site or a spacer element of similar size in the central exon, 26 nt upstream of the 5' splice site. The structure of each pre-mRNA is shown as Well as the splicing profile and the resulting mRNAs identified as products A*, B*, C* and D*. (B) The globin constructs were expressed in vivo following transfection in 293 cells. The expression plasmid pGST-MS2 is programmed to express the GST-MS2 protein via a CMV promoter. GST-MS2 expression was confirmed by RT-PCR analysis (not shown). Forty-eight hours post-transfection, total RNA was extracted and a RT-PCR assay was performed using a set of primers specific to exon 1 and exon 3. The position of the amplified products is shown as well as their identity relative to mRNA products. Some molecular weights markers and the expected sizes of the amplified products are indicated;

FIGS. 4A-F illustrate in vitro splicing interference with RNA oligonucleotides and protein-binding RNA oligonucleotides. (A) The position of the antisense RNA oligonucleotides on the C5' –/– pre-mRNA is shown. Oligo C5-5 is complementary to the 5' splice site of exon 7B, while the C5-M4 series are oligos complementary to the –4 to –23 sequence upstream of the 5' splice site of exon 7B. Oligo C5-M4A1 contains a DNA tail with the hnRNP A1 binding site TAGAGT (underlined), while oligo C5-M4A1W contains two RNA binding sites for A1 (underlined). Oligo C5-M4CT contains an unrelated 5' extension while oligo C5-M4 A1M contains mutated A1 binding sites. C5-M26 is complementary to the sequence located 26 to 45 nt upstream of the 5' splice site. C5-M26A1 contains an additional 5' DNA tail carrying an A1 binding site (underlined). (B) Native gel analysis of A1 binding to oligonucleotides. A shortened version of recombinant hnRNP A1 (GST-UP1) was used for testing binding affinity. Each labeled oligo was incubated with increasing amounts of GST-UP1 (0.5 and 1 µg). The TS10 oligo is a telomeric DNA oligo of 60 nt containing nine high-affinity A1 binding sites. Complexes were fractionated in a 5% acrylamide gel. The position of the free oligos and complexes is shown. (C) Pre-mRNAs were incubated in a HeLa extract for 2 hours in the presence of increasing amounts of oligonucleotides (0.01, 0.02, 0.05, 0.1, 0.5 pmoles in 12.5 µl reaction). The RNA was extracted and fractionated on a denaturing 11% acrylamide gel. The position of the pre-mRNAs, splicing intermediates and products is indicated. (D) Based on the results obtained in panel C, the relative use of proximal and distal splicing was compiled, expressed as a ratio of percentages and plotted relative to the amount of oligo used. (E) Labeled pre-mRNAs were incubated as above in the presence of increasing amounts of oligonucleotides (0.01, 0.02, 0.05, 0.1, 0.5 pmoles in 12.5 µl reaction). The RNA was extracted and fractionated on a denaturing 11% acrylamide gel. The position of the pre-mRNAs, splicing intermediates and products is indicated. (F) Labeled pre-mRNAs were incubated with increasing amounts of oligonucleotides (0.01, 0.02, 0.05, 0.1, 0.5 pmoles in 12.5 µl reaction). The position of the pre-mRNAs, splicing intermediates and products fractionated on a denaturing acrylamide gel is indicated;

FIGS. 5A-E illustrate splicing interference mediated by the protein-binding antisense oligo in vivo. (A) Splicing map of the Bcl-x pre-mRNA showing the splicing events leading to Bcl-xL and Bcl-xS mRNA production. The position and sequence of the 2'O-Me oligos used in vivo is indicated. (B) Native gel analysis of UP1 binding to oligonucleotides. The TS10 DNA oligo (60 nt) contains nine A1 binding sites. Each labeled oligo was incubated with increasing amounts of the shortened version of recombinant hnRNP A1 (GST-UP1). Complexes were fractionated in a 5% acrylamide gel. The position of the free oligo and the complexes is shown. In panels C, D and E, PC-3, HCT 116 and MCF-7 cells were transfected with increasing amounts of oligo. Total RNA was extracted after 48 hours and a RT-PCR assay was performed to evaluate the relative abundance of the Bcl-xS and Bcl-xL mRNA isoforms. The ratios of these amplified products are depicted in each graph and only RT-PCR results obtained at the 100 nM concentration are shown on gels stained with ethidium bromide;

FIGS. 6A-B illustrate the role of hnRNP A1/A2 in the activity of the interfering antisense oligo in HeLa cells. One set of transfections comprised HeLa cells mock-treated or treated with 100 nM of RNA oligo X-M4 and X-M4A1W. Another set of transfections was performed with the same oligos but was co-transfected with siRNAs, molecules specific for human hnRNP A1 and hnRNP A2. (A) The ratio of the Bcl-xL/Bcl-xS amplified products is plotted on the histogram. The ratios of these amplified products are depicted in the histogram; (B) Total RNA was extracted after 24 h and, a RT-PCR assay was carded out using Bcl-x-specific primers. A typical result is shown in the right panel.;

FIGS. 7A-B illustrate monitoring U1 snRNP binding to the proximal 5' splice site using an oligo-directed RNase H protection assay. (A) The C5-M26S pre-mRNA was incubated in, a mock-treated extract or an extract that had been depleted of U1 (U1Δ) by decapitation using a DNA oligo complementary to the 5' end of U1 RNA and RNase H. Splicing mixtures were incubated for the indicated times (in min) and a protection assay was performed with a DNA oligo complementary to the 5' splice site of exon 7B. (B) The C5' –/– RNA was incubated for the indicated times (in min) with interfering RNA oligos (C5-M4 or C5-M4A1W) in a HeLa nuclear extract. Following incubation, an oligo complementary to the proximal 5' splice site of exon 7B was added along with RNase H. The position of the fully protected pre-mRNA and molecules derived from the cleavage at the 5' splice site of exon 7B are shown;

FIGS. 8A-D illustrate that high-affinity binding sites for A1/A2 stimulate the in vitro removal of long introns:

Figure 2C:
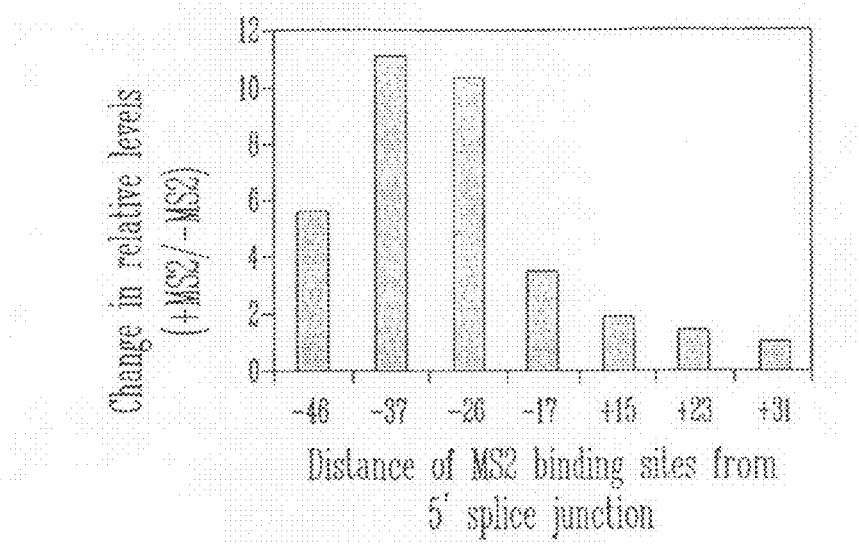

(A) Structure of the model pre-mRNAs. The size of the short introns in 7-Ad and 7B-Ad pre-mRNAs is indicated in nucleotides. The size of lambda inserts A, B and C are respectively 1015, 943 and 1038 nt. These inserts do not contain putative A/B binding sites matching the sequences UAGGGU/A or UAGAGU/A. The long intron substrates contain either exon 7 or exon 7B as first exon, and either the adenovirus L2 or the Bcl-X exon as second exon. When no other elements are inserted, the pre-mRNAs correspond to the (–.–) version. The (+.+) version contains ABS inserted 26 nt downstream of the 5' splice site and 88 nt upstream of the 3' splice site, whereas the (→.←) version contains inverted repeats at the same positions.

(B) The 7-Ad and 7B-Ad pre-mRNAs were co-incubated for the times indicated (in minutes) in a HeLa nuclear extract (lanes 1-6). Additional mixtures were prepared with pre-mRNAs carrying the 1015 nt-long lambda sequence A (7-AdA and 7B-AdA) lacking ABS (lanes 7-12) and containing ABS (lanes 13-18). The final concentration of each pre-mRNA was 80 pM. Following RNA extraction, the mRNA products from mixtures were amplified by RT-PCR, using a common set of primers (reverse primer complementary to the adenovirus sequence and forward primer corresponding to plasmid sequence downstream from the T3 RNA polymerase promoter found upstream of the exon 7 and 7B-specific sequences). The graph displays the abundance of splicing product amplified from the splicing reaction incubated for different times.

(C) Each of the long-intron 7-Ad pre-mRNAs carrying lambda inserts B or C (7-AdB or 7-AdC; 80 pM) was incubated with the short-intron 7B-Ad pre-mRNA (8 pM). Versions lacking (–.–) or containing (+.+) ABS, as well as carrying inverted repeats (→.←) were used. Following incubation for different times, spliced products were amplified by RT-PCR using a common set of primers. The co-incubated short-intron control is only shown for the 7-AdC pre-mRNA. M=molecular weight markers.

(D) Long-intron pre-mRNAs 7-BclA and 7B-BclA (80 pM each) lacking (–.–) or containing (+.+) ABS were co-incubated for the indicated times in a HeLa extract. M=molecular weight markers.

FIG. 9 illustrates the activity of a single ABS on long-intron splicing. The 7-AdA and 7-AdB pre-mRNAs lacking ABS ((–.–), lanes 1-4), containing two ABS ((+.+), lanes 13-16) or containing either only the downstream ((–.+), lanes 5-8) or the upstream ABS ((+.–), lanes 9-12) were mixed with the short-intron 7B-Ad pre-mRNA (control pre-mRNA) and incubated in a HeLa extract for the indicated times. The mRNA from all substrates was amplified by RT-PCR using common primers in the presence of 32P-dCTP. The short-intron 7B-Ad control pre-mRNA is only shown for 7-AdA. The graph displays the abundance of amplified products derived from the 7-AdA pre-mRNA at different incubation times.

FIGS. 10A-C illustrate that the hnRNP A1 protein stimulates long-intron splicing (A) Removal of hnRNP A/B proteins affects long-intron splicing. The long-intron substrate 7-AdB lacking ABS (–.–) or containing ABS (+.+) was co-incubated with the short-intron 7B-Ad control pre-mRNA (80 and 8 pM, respectively) in a HeLa extract for 90 min in the presence of increasing amounts of the telomeric oligonucleotide TS10 (0, 80, 160, 320, 640 nM, respectively).

(B) Splicing mixtures were incubated with increasing amounts of recombinant GST-A1 protein (0, 0.8, 1.6 and 3.2 μM). The 7-AdB pre-mRNA carrying inverted repeats (→.←) was also used (C) Splicing mixtures were incubated with recombinant GST-A1 protein or His-tagged A1 protein (1 μg each).

FIGS. 11A-F illustrate that a protein-binding oligonucleotides carrying ABS stimulate the splicing of long introns:

(A) Schematic representation of model long-intron pre-mRNAs and the position and structure of the RNA oligonucleotides.

(B) The 7-AdA pre-mRNAs lacking ABS (–.–) or containing ABS (+.+) were incubated in a HeLa extract in the absence (lanes 1 and 4, respectively) or in the presence (lanes 2-3 and 5-6, respectively) of UA and Da oligonucleotides (8 and 20 nM of each oligonucleotide). The 7-AdB pre-mRNA (–.–) was also incubated in the presence of UA, and Da oligonucleotides (20 nM each). In lanes 1-8, the short-intron 7B-Ad pre-mRNA was co-incubated with all 7-Ad long-intron pre-mRNAs as an internal splicing control. In lanes 9-13, the 7B-AdA pre-mRNA lacking ABS was co-incubated with the short-intron 7-Ad in the presence of various concentrations of UA and Da oligonucleotides (0, 8, 80 and 800 pM of each oligonucleotide) or the UA oligo alone (800 pM). Incubation in HeLa extracts was for 60 minutes.

(C) The 7-AdA pre-mRNA was co-incubated with the short-intron 7B-Ad pre-mRNA in a HeLa nuclear extract for 90 minutes at 30° C. Each oligonucleotide was used at a concentration of 160. Cis (lane 7) indicates that the 7-AdA pre-mRNA was the (+.+) version containing two ABS. Quantification of the results for each lane is provided in the histogram.

(D) The 7-AdB pre-mRNA was co-incubated with the 7B-Ad control pre-mRNA and either the UB or UBn oligonucleotide (40 nM each). UBn carries a non-ABS tail. Incubation was for 60 minutes in a HeLa extract.

(E) The 7B-BclA was co-incubated with 100-fold less of the short-intron 7-Ad control pre-mRNA and increasing amounts of the UB and Db oligonucleotide mixture (0, 2, 4, 10, 20 and 40 nM) or with 40 nM of individual or mixtures of various oligonucleotides.

(F) The 7-BclB pre-mRNA was co-incubated with 100-fold less of the short-intron 7B-Ad pre-mRNA for 60 min in the presence of increasing amounts of the UB and Db oligonucleotides (0, 0.8, 8, 40 and 80 nM each, or 80 nM of each of oligonucleotide for 60 min at 30° C. Cis (lane 9) indicates that the 7-BclB pre-mRNA is the (+.+) version with two ABS. Histogram representing the quantitation of the splicing results obtained with the 7-BclB pre-mRNA; and FIG. 12 illustrates that a protein-binding oligonucleotides carrying ABS can modulate alternative splicing in vitro. A uniformly labeled pre-mRNA carrying the competing 5' splice sites of exon 7 and exon 7B from the murine hnRNP A1 gene was incubated in a HeLa nuclear extract for 90 min at 30° C. in the absence or in the presence of protein-binding oligonucleotides. Increasing amounts of UST and Da oligonucleotides were used (0, 0.08, 0.8, 8, 80 and 160 nM of each). 160 nM of each oligonucleotide was used for the rest. The structure of the pre-mRNA and the position of hybridization of the oligonucleotides are shown on top. The products of the splicing reaction were resolved in a 10% acrylamide/8 M urea gel. The position of the lariat products that migrate above the pre-mRNA and derived from the use of the proximal (7B) or distal (7) 5' splice site are shown.

DETAILED DESCRIPTION OF THE INVENTION

In accordance with the present invention, there is provided novel methods for interfering with and influencing splice site selection. The ability to modulate or interfere with splice site selection is useful not only as a tool to study alternative splicing but also as a therapeutic agent for diseases such as cancer where alternative splicing is associated with the pathogenesis of the disease.

In general, this invention is based on the discovery that an oligonucleotide containing a protein binding site extension and sequences complementary to sequences upstream of a splice site (e.g., in the exon preceding a 5' splice site) can block splicing at this splice site. In addition, oligos containing binding sites for hnRNP A1/A2 can be used to remodel intron and pre-mRNA structure to facilitate the removal of long introns or to affect alternative splice site use. These methods can be used to study the function of different protein isoforms, to prevent the usage of an aberrant splice site and to reprogram alternative pre-mRNA splicing.

Oligonucleotides

The present invention features the use of oligonucleotides to interfere with splice site selection. The oligonucleotides are generally composed of two distinct regions: (i) a nucleic acid sequence element that is complementary to the region of the pre-mRNA being targeted, and (ii) an extension containing a protein binding site sequence element which is recognized by a protein that binds to single-stranded or double-stranded nucleic acid molecules. In this way, the oligonucleotide can direct the binding of a protein or a protein/nucleic acid complex to the vicinity of a splice site. The oligonucleotide can also serve to block binding of a splicing factor to the splice site and inhibit splicing in this manner.

The oligonucleotides described herein can be DNA or RNA and include any modifications. Such modifications can improve the oligonucleotide in a variety of ways including improved stability, resistance to degradation by exo- and endo-nucleases, or delivery of the oligonucleotide to a cell. Examples of modified oligonucleotides include modifications to the phosphate backbone such as methyl phosphonates, methyl phosphonothioates, phosphoromorpholidates, phosphoropiperazidates and phosphoramidates. In one example, every other one of the internucleotide bridging phosphate residues may be modified as described. In another non-limiting example, such oligonucleotides are oligonucleotides wherein at least one, or all, of the nucleotides contain a 2' loweralkyl moiety (e.g., C1-C4, linear or branched, saturated or unsaturated alkyl, such as methyl, ethyl, ethenyl, propyl, 1-propenyl, 2-propenyl, and isopropyl). The modified oligonucleotide can also contain a modified backbone such as a morpholino backbone or a peptide nucleic acid (PNA) backbone wherein the deoxyribose phosphate skeleton has been replaced by a peptide oligomer (See U.S. Pat. Nos. 5,142,047; 5,185,444; 5,539,082; 5,977,296;. 6,316,595; 5,719,262; 5,766,855; 5,714,331; 5,705,333; 5,034,506; and International Patent No. WO92/20703).

Additional modifications of the oligonucleotides described herein include the modification of at least one sugar moiety. Examples of modified sugar moieties include but are not limited to 2'-O-Methyl and 2'-O-Methooxyethyl groups. Chimeric oligonucleotides, or oligonucleotides containing a mixture of chemistry (e.g. 2'-O-methyl phosphorothioate), are also included. Also included are oligonucleotides with cytidines 5' to guanosines replaced with 5-methylcytidine in order to reduce the so-called CpG effect.

The complementary portion of the oligonucleotide contains sequences that are substantially complementary to the region of the pre-mRNA being targeted. It is preferable that this portion of the oligonucleotide be RNA or modifications thereof (e.g., 2'-O-Methyl phosphorothioate, 2'-O-Methooxyethyl phosphorothioate, morpholino and PNA backbones). The oligonucleotide is at least 70% complementary to the nucleotides in the region of the pre-mRNA being targeted, preferably at least 85%, more preferably at least 90%, and most preferably at least 95% complementary. In general, the oligonucleotide is directed to a region at least eight base pairs in length upstream of a splice site via this complementary portion. This region begins preferably 1 to 46 base pairs upstream of the splice site, more preferably 16 to 36 base pairs upstream, and most preferably 20 to 26 base pairs upstream of the splice site. The splice site can be the 5' or the 3' splice site of any given intron/exon boundary; the 5' splice site is the preferred target.

The second portion of the oligonucleotide is the extension containing a binding site for a protein that can bind single-stranded nucleic acid molecules. This extension can be single-stranded DNA or RNA or any modifications thereof (e.g., 2'-O-Methyl phosphorothioate, 2'-O-Methooxyethyl phosphorothioate, morpholino and PNA backbones). The protein binding site sequence element binds a protein that is selected from any art-known single-stranded or double-stranded nucleic acid binding proteins. There are many examples of such proteins some of which include the SR family of proteins, hnRNP proteins, and RNA binding proteins such as U2AF and TAR proteins. The ability of the extension to bind a particular protein can be determined by standard protein-nucleic acid binding assays such as electrophoretic mobility shift assays (EMSA) using a radioactively labeled form of the oligonucleotide.

In addition, the extension can include the RNA sequences of any known snRNA, snoRNA or other small RNA, which is known to interact with proteins and to form an RNA/protein complex. Non-limiting examples include U1-U6, U8, U14, U22, snR30, 5SRNA, and the RNA subunit of telomerase. In this way, the extension would direct the binding of the RNP to sequences upstream of the splice site which would then interfere with splicing.

Methods for the synthesis of oligonucleotides and modified forms of oligonucleotides are well known to those of skill in the art using biological, enzymatic, and chemical means. For example one preferred method of synthesis is solid phase synthesis which is described in the following U.S. patents, each incorporated herein by reference: U.S. Pat. Nos. 5,539,082; 5,373,053; 5,258,454; 4,507,230; and 4,631,211.

Protein-binding custom-made RNA oligonucleotides were purchased from Dharmacon Research Inc. (Lafayette, Colo., USA). The 3' half of the upstream oligo UA or UB is complementary to the intronic sequences at the 5' end of the lambda insert A or B, respectively, 42 nt downstream from the 5' splice site. These oligos have a CE1a element sequence at the 5' end portion. On the other hand, oligos UOA and UOB contain the same complementary sequences but CE1a element is located at the 3' end. The downstream oligos Da and Db are complementary to a 20 nt region 67 nt upstream of the adenovirus exon L2, and 122 nt upstream of the Bcl-X exon 3, respectively. These oligos contain the CE1a element sequence in their 3' end portion. The upstream oligo UB1 is complementary to a 20 nt region in insert B, 489 nt downstream of the 5' splice site of exon and contains the CE1a element in its 5' end portion. Oligo UB2 has the CE1a element in the 3' end portion and carries a 20 nt region complementary to a sequence in insert B which is 559 nt downstream from the 5' splice site. Oligo UBn shares its last 19 nucleotides with oligo UB but has a non-ABS 25 nt-long tail at its 5' end. Oligo UST has a 20 nt at the 3' end complementary to the intronic sequences between the distal and the proximal 5' splice sites in RNA 53 while the 5' portion of this oligo contains the CE1a element. Oligo DST hybridizes 125 nt upstream of the 3' splice site of the adenovirus 3' splice site and carries a CE1a element. The sequences of all oligos used in splicing are shown in Table 2. In Table 2, the complementary sequences are underlined, whereas the CE1a element is in bold. The non-ABS extension of UBn and USn is shown in small case letters.

The DNA primers used for the RT-PCR amplification of spliced products were the 20 nt-long E-Ad and BclX3 which used as the downstream primers for the RT step and the PCR amplification of products carrying the adenovirus or Bcl-X as second exon, respectively. E-Ad (5'-GAGTTTGTCCT-CAACCGCGA-3' (SEQ ID NO:15)) is complementary to the 5' end of the adenovirus exon L2. BclX3 (5'-TCGGCTGCT-GCATTGTTCCC-3' (SEQ ID NO:16)) is complementary to a region 21 nt downstream of the 5' end of the Bcl-X exon 3. The upstream primer in all amplifications was a 21 nt-long oligo T3-5' (5'-GGGAACAAAAGCTGGGTACCG-3' (SEQ ID NO:17)) that hybridizes to the 5' end region of all transcripts synthesized from the T3 RNA polymerase promoter.

TABLE 2

RNA oligonucleotides used in splicing experiments

| Oligo | Length (nt) | Sequence (5'-3') |
|---|---|---|
| UA | 40 | GGGUACCUUUAGAGUAGGCCCGCUGCGUGA GUAUCCGUGA (SEQ ID NO: 18) |
| UB | 40 | GGGUACCUUUAGAGUAGGCCUCGGCUUGGU GUUCUUUCAG (SEQ ID NO: 19) |
| UOA | 40 | CGCUGCGUGAGUAUCCGUGAGGGUACCUUUA GAGUAGGCC (SEQ ID NO: 20) |
| UOB | 40 | GCGGCUUGGUGUUCUUUCAGGGGUACCUUU AGAGUAGGCC (SEQ ID NO: 21) |
| UB1 | 40 | GGGUACCUUUAGAGUAGGCCUGAUUCUCGCU GUCAGAGGC (SEQ ID NO: 22) |
| UB2 | 40 | GAUUCCUCUGCUGGCCAGGAGGGUACCUUUA GAGUAGGCC (SEQ ID NO: 23) |
| UBn | 45 | guucgaucucguaacgaaggcguaCGGCUUG GUGUUCUUUCAG (SEQ ID NO: 24) |
| Da | 40 | GACGUGCAGGUCAAGCUUGAGGGUACCUUUA GAGUAGGCC (SEQ ID NO: 25) |
| Db | 40 | CUCUGGGCCAGGUAAAGGGCGGGUACCUUUA GAGUAGGCC (SEQ ID NO: 26) |
| UST | 40 | GGGUACCUUUAGAGUAGGCCUCCUGUCCACC AGGGCUGCA (SEQ ID NO: 27) |
| USn | 45 | guucgaucucguaacgaaggcguaGCUGUCC ACCAGGGCUGCACC (SEQ ID NO: 28) |
| DST | 40 | CCUUCACCCAGGCUGUGCCGGGUACCUUUA GAGUAGGCC (SEQ ID NO: 29) |

Purification of Proteins

The oligonucleotides of the present invention contain a complementary portion and a protein binding site extension. This protein binding site sequence element can direct the binding of a protein known to be present in the cell or cell extract being used. In addition, the protein can be a protein that is not found in the cell or cell extract and must be supplied exogenously. This variation allows for more control of the splice site interference as the protein can be added only when splice site interference is desired.

In this application, the protein is purified using art-known methods of protein production and purification. Examples of such methods include the use of bacterial or insect cells for the production of the protein (e.g., *E. Coli* and Sf9 cells, respectively) and affinity chromatography for purification for use in in vitro systems. Common techniques include GST protein purification, His-tagged protein purification, and baculovirus protein production and purification, all of which are known methods to a skilled artisan.

Recent advances have been made for the delivery of purified proteins directly to mammalian cell cultures or to mammals. These techniques involve the use of protein transduction domains (PTDs), which can be fused to the protein of interest. Protein transduction domains are small peptide fragments that have the capacity to cross both cytoplasmic and nuclear membranes, allowing the direct introduction of proteins into cells. Examples of proteins containing protein transduction domains include the HIV TAT protein, HSV VP22 protein, the *Drosophila* Antennapedia homoedomain protein, and highly basic peptides such as poly-lysine or poly-arginine peptides. In preferred embodiments of the invention, the PTD is a short segment of any of the above described proteins or any additional proteins shown to facilitate translocation of heterologous proteins. For example, amino acids 47-57 of the TAT protein has been used to effectively transduce fluorescein and beta-galactosidase into mouse cells by direct linking of the PTD tag to the protein. In another, commercially available example, a 16 amino acid peptide corresponding to the DNA-binding domain of the *Drosophila* antennapedia homeodomain is used to transduce proteins to the cytoplasm and nucleus of living cells (Trans-Vector System, Qbiogene, Inc).

For the present invention, the desired protein is linked to a PTD using a bacterial expression vector. The fusion protein is purified from bacterial cells using either soluble or denaturing conditions. The purified fusion protein is added to mammalian cell culture or injected in vivo into an animal. Protein transduction occurs in a concentration dependent manner and can take as little as five minutes. Additional methods for generating PTD-protein fusion proteins include peptide synthesis of the desired fusion protein or transfecting mammalian cells using a recombinant vector for expression of the fusion protein. The fusion protein then transduces from the primary transfected cells into the surrounding cells.

Introduction of Oligonucleotides into Cells

A variety of methods are available for transfection, or introduction, of oligonucleotides into mammalian cells. The most effective delivery system known to date is cationic lipids. There are also several commercially available transfection reagents. These include, for example, TransIT-TKO™ (Mirus, Cat. # MIR 2150), Transmessenger((Qiagen, Cat. # 301525), and Oligofectamine™ (Invitrogen, Cat. # MIR 12252-011). Protocols for each transfection reagent are available from the manufacturer.

Retroviral vectors, adenoviral vectors, adeno-associated viral vectors, or other viral vectors with the appropriate desired tropism for cells may be used as a gene transfer delivery system for the methods of the present invention. Numerous vectors useful for this purpose are generally Plasmids The short intron pre-mRNA substrates 7-Ad and 7B-Ad were transcribed from plasmids p01[7-Ad (−)] and p45.1[7B-Ad (−)], respectively using the T3 RNA polymerase promoter. p01 was produced by deleting a 188 nt BamHI-EcoRI fragment from p104.2 [C3' (−.−)] followed by blunt end formation using the Klenow enzyme. Construction of p104.2 (Blanchette and Chabot, (1999), EMBO J, 18:1939-1952) and p45.1 has been described previously. Short intron pre-mRNAs containing the 3' splice site of the Bcl-X exon 3 were similarly generated from p232[7-BclX(−)] and p203 [7B-BclX (−)]. p203 and p232 were produced by replacing a 517 nt HindIII-NaeI fragment of p45.1 and p01, respectively, with a 345 nt HindIII-SmaI fragment from a human Bcl-X plasmid.

Three lambda DNA fragments, approximately 1 Kb-long, were used as spacers to generate long introns. These fragments were obtained from intermediate clones pNSL5.1 and pNSL6.1 as follows. pNSL5.1 and pNSL6.1 were constructed by inserting either the 2263 bp-long NruI-ScaI (nt 16423-18686) or the 3653 bp-long NruI-ScaI (nt 28052-31705) lambda DNA fragment in reverse orientation in the EcoRV site of the K+ vector backbone, respectively. pNSL5.1 was then digested using BsaAI and PvuII to generate a 1015 bp fragment (insert A) or NaeI and HincII to obtain a 1038 bp fragment (insert C). pNSL6.1 was digested using EcoRV and SspI to produce a 943 bp fragment (insert B).

p189 [7-AdA(−.−)], was obtained by replacing the 142 bp SmaI-EcoRV fragment of p45 with the 1015 bp lambda insert A. To produce p190[7-AdA(+.+)], the same fragment was cloned in the EcoRV site of an intermediate plasmid p36.2BRL. Construction of p36.2BRL involved deletion of a 269 bp BamHI-BamHI-EcoRI portion followed by insertion of an 18-bp BamHI-EcoRI Linker (BRL) adapter composed of two complementary B and R oligos. Oligo B (5'-GATC-CGGCCGATATCGCG-3' (SEQ ID NO:30)) has a 4 nt overhang complementary to the BamHI site while the oligo R (5'-AATTCGCGATATCGGCCG-3' (SEQ. ID NO:31)) has a 4 nt overhang complementary to the EcoRI site. p191.[7-AdA(→.←)] was produced by replacing the 142 bp SmaI-EcoRV fragment of p153 (Nasim et al., 2002) with the 1015 bp insert A. Incorporation of the 943 bp insert B or the 1038 bp insert C resulted in the generation of p186[7-AdB(−.−)], p187[7-AdB(+.+)], p188[7-AdB(→.←)] and p174[7-AdC(−.−)], p175[7-AdC(+.+)], p176[7-AdC(→.←)], respectively.

Construction of p205[7B-AdB(−.−)] and p206[7B-AdA(−.−)] was accomplished by incorporating the 943 bp insert B or the 1015 bp insert A at the EcoRV site of p45.1, respectively. p209[7B-AdB(+.+)] and p210[7B-AdA(+.+)] were obtained through a two-step strategy. In the first step, an intermediate plasmid p202 [7B-Ad(+.+)BRL] was constructed by replacing a 105 bp EcoO1091-SmaI fragment of p36.2BRL with a 157 bp EcoO1091-EcoRV fragment from p45.1. This was followed either by replacement of a 51 bp BamHI-HindIII fragment of p202 with a 995 bp BamHI-HindIII fragment from p187 to produce p209, or incorporation of the 1015 bp insert A in the EcoRV site of p202 to obtain p210.

p194[7-BclB(−.−)] and p198[7-BclB(+.+)] were constructed by replacing a 195 bp HindIII-SacI fragment of p186 and p187, respectively, with a 387 bp HindIII-SacI fragment from pK+bclx 5'/3'short. On the other hand, p195[7-BclA(−.−)] and p199[7-BclA(+.+)] were constructed by replacing a 572 bp EcoO1091-HindIII fragment of pK+bclx 5'/3' short with the 1126 bp EcoO1091-HindIII fragment from p189 and the 1184 bp EcoO1091-HindIII fragment from p190, respectively.

To construct p211[7B-BclB(−.−)] and p212[7B-BclA(−.−)], the 519 bp HindIII-NaeI fragment in p205 and p206 was replaced with the 288 bp HindIII-NaeI fragment from pK+bclx 5'/3' short. Corresponding ABS containing plasmids p214[7B-BclB(+.+)] and p21 5-[7B-BclA(+.+)] were constructed as follows. The 117 bp EcoRV-SphI fragment in p203 was replaced with the 1136 bp SmaI-SphI fragment of p198 to get p214 whereas construction of p215 was achieved in two-steps. First, the 92 bp XhoI-SmaI portion of p204 was replaced with a 148 bp XhoI-EcoRV fragment from p45.1 to generate an intermediate p213[7B-BclX(+/+)BRL]. Second, the 1015 bp insert A was subcloned at the EcoRV site of p213 to produce p215.

The 953 bp and 995 bp BamHI-HindIII fragments from p186 and p187, respectively, were swapped to generate p186.2[7-AdB(−.+)], containing a single A1 binding site (ABS) near the 3' splice junction, and p186.3[7-AdB(+.−)], the plasmid containing a single ABS near the 5' splice junction. Likewise, p189.2[7-AdA(−.+)] and p189.3[7-AdA(+.−)] were constructed by swapping the 769 bp EagI-BsaAI fragment of p189 and the 798 bp fragment of p190 with one another.

Transcription and Splicing Assays

Constructs containing adenovirus exon L2 were linearized with ScaI whereas the constructs containing Bcl-X exon 3 were linearized using BgII, and used as templates for in vitro transcription. In general, minimally labeled pre-mRNA substrates were synthesized in vitro using T3 RNA polymerase and gel-purified as described earlier. Labeling was done for the quantification purpose only. A known amount of the pre-mRNA was then incubated in HeLa nuclear extract under standard splicing conditions at 30° C. The RNA material was then PCA extracted and ethanol precipitated. To investigate the effect of protein-binding RNA oligos on splicing, pre-mRNA molecules were mixed with either the individual oligo or a mixture of the oligos prior to splicing. RNA species obtained after splicing were quantitated and resuspended in sterile water to a concentration of 5-10 atomoles per µl. An equivalent amount of this solution was then subjected to RT-PCR amplification. To analyze alternative pre-mRNA splicing, a uniformly labeled pre-mRNA was synthesized and processed as described earlier.

RT-PCR

The pre-mRNAs incubated in splicing extracts were minimally labeled such that the amount of pre-mRNA used could be precisely quantitated and followed until after PCA extraction and ethanol precipitation. In many experiments, a short-intron pre-mRNA was co-incubated with the test pre-mRNA to insure equivalent processing and loading between different samples. In some experiments, RNA controls were added only before the RT-PCR reaction. Amplification protocols used the ready-to-go RT-PCR beads (Amersham Pharmacia Biotech) as described earlier. In several experiments, amplifications were performed in the presence of 32P-labeled dCTP. The reaction mixtures after amplification were treated with RNase A and the products were resolved on a 5% non-denaturing acrylamide gel, unless stated otherwise. The gel was stained with ethidium bromide, photographed under UV light and quantitated using QuantityOne software (Bio-Rad). When amplified products were 32P-labeled, products were quantified on an InstantImager (Canberra-Packard) and then exposed on film by autoradiography.

Uses

The methods of the present invention are used generally to (1) address the function of different protein isoforms made by alternative splicing, (2) prevent the usage of aberrant splice sites, and (3) reprogram alternative pre-mRNA splicing.

The methods of the present invention are useful as in vitro or in vivo tools to examine splicing in human or animal genes that are developmentally and/or tissue regulated.

The methods of the present invention are also useful as a tool to examine the function of various isoforms of a given protein. In one example, the method is used to create an isoform of a protein that behaves in a dominant negative manner. This dominant negative protein can then inhibit the function of the protein. For example, the expression of an alternative isoform of the human telomerase gene product can inhibit telomerase activity in telomerase positive cells.

The methods of the present invention are also useful as therapeutic agents in the treatment of diseases involving aberrant splicing. Examples of such diseases include but are not limited to thallassemia, haemophilia, retinoblastoma, cystic fibrosis, analbuminemia, and Lesch-Nyhan syndrome. Table 3, taken from a recent review by Caceres and Kornblihtt summarizes examples of hereditary disorders caused by exonic point mutations that affect alternative splicing (Trends in Genetics, 18:186-193, 2002).

TABLE 3

The effects of alternative splicing on disease[a]

| Disorder | Gene | Missense | Nonsense | Translationally Silent |
|---|---|---|---|---|
| Acute intermittent porphyria | Porphobilinogen deaminase | | | R28R(C→G, 3) |
| Breast and ovarian cancer | BRCA1 | | E139K(G→T, 18) | |
| Carbohydrate-deficient glycoprotein syndrome type 1a | PMM2 | | E139K(G→A, 5) | |
| Cerbrotendinous xanthomatosis | Sterol-27-hydroxylase | | | G112G(G→T, 2) |
| Cystic fibrosis | CFTR | | E60X(G→T, 3) R75X(C→T, 3) R553X(C→T, 11) W1228X(G→A, 20) | |
| Ehlers-Danlos syndrome type VI | Lysyl hydroxylase | | Y511X(C→A, 14) | |
| Fanconi anemia | FANCG | | Q356X(C→T, 8) | |
| Frontotemporal dementia (FTDP-17) | Tau | S305N(G→A, 10) | | L284L(T→C, 10) |
| | | N297K(T→G, 10) | | S305S(T→C, 10) |
| Hemophilia A | Factor VIII | | E1987X(G→T, 19) R2116X(C→T, 22) | |
| HPRT deficiency | Hypoxanthine phosphoribosyl transferase | G40V(G→T, 2) R48H(G→A, 3) A161E(C→A, 6) P184L(C→T, 8) D194Y(G→A, 8) E197K(G→A, 8) E197V(A→T, 8) | | |
| Leigh's encephalomyelopathy | Pyruvate dehydrogenase E1α | | | G185G(A→G, 6) |
| Marfan syndrome | Fibrillin-1 | | | I2118I(C→T, 51) |
| Metachromatic leukodystrophy (juvenile form) | Arylsulfatase A | T4091(C→T, 8) | | |
| Neurofibromatosis type 1 | NF1 | | R304X(C→T, 7) Q756X(C→T, 14) Y2264X(C→A, 37) | |
| OCT deficiency | Ornithine carbamoyltransferase | | L304F(G→T, 9) | |

TABLE 3-continued

The effects of alternative splicing on disease[a]

| Disorder | Gene | Missense | Nonsense | Translationally Silent |
|---|---|---|---|---|
| Porphyria cutanea tarda | Uroporphyrinogen decarboxylase | | | E314E(G→A, 9) |
| Sandhoff disease | Hexosaminidase | P404L(C→T, 11) | | |
| Severe combined immunodeficiency | Adenosine deaminase | R142Q(G→A, 5) | R142X(C→T, 5) | |
| Spinal muscle atrophy | SMN1 | | W102X(G→A, 3) | |
| Spinal muscle atrophy | SMN2 | | | F280F(C→T, 7) |
| Tyrosinemia type 1 | Fumaryl acetoacetate hydrolase | Q279R(A→G, 8) | | |

[a]Missense, nonsense, and translationally silent point mutations that cause hereditary disease through changes in the alternative splicing of the exons that harbor them. Notation: S305N(G→A, 10) indicates that a G mutated to an A in exon 10, with a putative translational effect of replacing a serine at position 305 for an asparagines. Consistently E60X(G→T, 3) indicates that a G mutated to a T in exon 3, with a putative translational effect of generating a premature stop codon instead of the codon for glutamic acid position 60.

In addition to the therapeutic uses of the present invention for the treatment of the above-mentioned genetic diseases, the invention can be used as a treatment for cancer. The oligonucleotides can be used to shift splice site utilization towards the production of mRNA isoforms that encode pro-apoptotic proteins instead of anti-apoptotic proteins, and in doing so promote cell death. For example, inclusion of exon 6 in the Fas receptor pre-mRNA produces a membrane-bound form that acts as an effector of apoptosis. In contrast, skipping exon 6 yields a soluble form that inhibits programmed cell death. Likewise, Bcl-x is alternatively spliced to produce Bcl-xL and Bcl-xS, which inhibits and activates apoptosis, respectively. Similar examples have been documented with Mcl-1, Bok, CC3 and caspases 1, 2, 6 and 7. Alternative splicing of the pre-mRNA is responsible for the production of these forms. Targeting splice sites responsible for the production of the anti-apoptotic form with oligonucleotides carrying a protein binding site extension would allow for a shift towards the production of the pro-apoptotic form. This approach can be used to promote cell death and kill cancer cells.

Alternatively, the oligonucleotides can be used to block the production of various oncogenic spliced variants of proteins involved in cancer. For example, increased skipping of the alpha exon in glioblastoma produces a fibroblast growth factor receptor with higher affinity for ligands. In another example, the inappropriate inclusion of exons in BIN1 mRNA results in the loss of tumor suppressor activity in some melanoma samples. Alternative splicing can also generate isoforms of proto-oncogenes that are less active or that even display dominant negative activity, as is the case with a recently discovered isoform of the human telomerase hTERT which inhibits telomerase activity when expressed in telomerase positive cells. Other examples include naturally occurring mutations that promote the inclusion of the alternate IDX exon in H-ras mRNA to yield a ras oncoprotein with reduced oncogenic activity, and the p53 homologue p63 which undergoes complex alternative splicing to yield proteins with widely divergent biological properties. The methods of the present invention can be used to inhibit the production of the more oncogenic forms of these and any other proteins involved in cancer.

Another potential use for the methods and compositions described herein is for the treatment of a variety of neurological disorders associated with an imbalance in the production of different spliced isoforms of neuronal proteins. Examples of such disorders include schizophrenia, frontotemporal dementia, and amyotrophic lateral sclerosis.

Neural cell adhesion molecule (N-CAM) is a specific example of a protein that can be expressed as multiple isoforms and alterations in the relative levels of expression of each isoform is associated with neurological disorders including schizophrenia. NCAM is alternatively spliced to produce a short and long form (NCAM 140 and NCAM 180). NCAM 180 results from the specific inclusion of exon 18. NCAM 180 is essential for the differentiation of neuronal cells (dendrite formation). Therefore, oligonucleotides of the present invention can be used to prevent exon 18 inclusion, hence modulating isoform expression of NCAM and potentially blocking neuronal differentiation.

The methods of the present invention are also useful for controlling viral infection. For example, HIV produces more than 40 distinct mRNAs through alternative pre-mRNA splicing. Proper and efficient splicing is crucial at the initial stage of an HIV infection. Therefore, targeting HIV splice sites and preventing proper and efficient splice site utilization could prevent progression of the infection.

The present invention provides for the use of oligonucleotides having the characteristics set forth above for the preparation of a medicament for regulating gene expression in a patient afflicted with a disorder caused by aberrant splicing, as discussed above. In the manufacture of a medicament according to the invention, the oligonucleotide is typically admixed with, inter alia, an acceptable carrier. The carrier must, of course, be acceptable in the sense of being compatible with any other ingredients in the formulation and must not be deleterious to the patient. The carrier may be a solid or a liquid. One or more oligonucleotides can be incorporated in the formulations of the invention, which may be prepared by any of the well-known techniques of pharmacy consisting essentially of admixing the components, optionally including one or more accessory therapeutic ingredients.

In the formulation, the oligonucleotide may be contained within a lipid particle or vesicle, such as a liposome or microcrystal, which may be suitable for parenteral administration. The particles may be of any suitable structure, such as unilamellar or plurilamellar, so long as the antisense oligonucleotide is contained therein. Positively charged lipids such as N-[1-(2,3-dioleoyloxi)propyl]-N,N,N-trimethyl-amonium-methylsulfate, or "DOTAP," are particularly preferred for such particles and vesicles. The preparation of such lipid particles is well known. See, e.g., U.S. Pat. Nos. 4,880,635; 4,906,477; 4,911,928; 4,917,951; 4,920,016; and 4,921,757, all of which are herein incorporated by reference).

The dosage of the oligonucleotide administered will depend upon the particular method being carried out, and when it is being administered to a subject, will depend on the disease, the condition of the subject, the particular formulation, and the route of administration. In general, intracellular concentrations of the oligonucleotide ranging from 0.005 to 50 μM, or more preferably 0.02 to 5 μM, are desired. For administration to a subject such as a human, a daily dosage ranging from about 0.001 to 50 mg/Kg, more preferably 0.01 to 10 mg/Kg, and most preferably 0.1 to 5 mg/Kg is employed.

EXAMPLES

Example 1

Effects of Splice Site Interference Using Oligonucleotide Versus Protein Binding To determine the relative ability of oligonucleotide binding versus directed protein binding to interfere with splice site selection, an in vitro splicing assay was developed in HeLa cell extracts. This assay utilized a model pre-mRNA substrate (hereafter referred to as "553 or C5' −/− pre-mRNA") containing competing 5' splice sites taken from hnRNP A1 exon 7 and exon 7B. The 553 pre-mRNA was radioactively labeled with $^{32}$P and incubated in a HeLa nuclear extract for two hours, and then total RNA was isolated and fractionated on acrylamide/urea gels. Oligonucleotides were resuspended in water and added to the splicing mixtures containing extracts and target pre-mRNA at indicated concentrations. Normally, the pre-mRNA was spliced predominantly to the internal (proximal) 5' splice site of exon 7B. However, if the proximal 5' splice site was somehow blocked, then the distal site from exon 7 was used. Distal lariat molecules migrated above the pre-mRNA while proximal lariat molecules migrated below the pre-mRNA. This assay was used to measure the blocking ability of a given oligonucleotide.

The applicants first determined that an oligonucleotide that bound to sequences 26 to 46 nucleotides upstream of a 5' splice site did not repress splicing as efficiently as an oligonucleotide directly targeting the 5' splice site (FIG. 1, compare oligo A and oligo B). Sequences of oligonucleotides were as follows: A: 5'-UAC CUA CCA CUA CCA CCG-3' (SEQ ID NO: 32) and B: 0.5'-CCU CCU CCG UUG UUA UAG-3' (SEQ ID NO: 33). Oligonucleotides were 2'-O-Me derivatives.

The applicants also determined that targeting the binding of a protein to sequences between 26 and 46 nucleotides upstream of a 5' splice site was more efficient at reducing the use of this 5' splice site than targeting an oligonucleotide to this region. (FIG. 1, lane 5). For this experiment, a model pre-mRNA containing a binding site for MS2, a bacteriophage coat protein, in the vicinity of the proximal 5' splice site was incubated in a HeLa nuclear extract in the presence of purified GST-MS2. The MS2 coat protein had a very strong affinity for its cognate site (Kd=1 nM). Importantly, targeting the −20 region of the pre-mRNA with a protein was more effective than targeting the same region with an oligonucleotide, possibly because the protein prevented 5' splice site recognition by U1 snRNP. In contrast, the oligonucleotide only interfered with a later step of spliceosome assembly. Thus, directed protein binding 20 nucleotides from the proximal 5' splice site led to a shift in favor of the distal 5' splice site.

Example 2

Effect of Protein Binding at Different Positions

The effect of targeting the binding of a protein in the vicinity of a 5' splice site with the goal of interfering with its use through steric hindrance was also tested. Although a few natural cases of this type of splicing control exist, it was intended to ascertain the parameters that are associated with such an effect using a pre-mRNA that contain two competing 5' splice sites. Using the C5'−/− pre-mRNA derived form the hnRNP A1 gene, the effect of targeting the binding of the bacteriophage MS2 coat protein close to the proximal 5' splice site was tested. A high-affinity MS2 binding site was inserted at various positions (−46, −37, −26, −17, +15, +23 and +31) upstream or downstream of the proximal 5' splice junction (FIG. 2A) and the in vitro splicing of the resulting pre-mRNAs was carried out in a HeLa extract supplemented in the presence or the absence of the recombinant GST-MS2 protein. As seen in FIG. 2B, positioning GST-MS2 binding 26 nt upstream of the proximal 5' splice site promoted a decrease in the use of the proximal 5' splice site and a strong increase in the use of the distal 5' splice site, (compare lane 4 with, lane 3). GST-MS2 did not affect 5'splice site utilization when the MS2 binding site was substituted for its complementary sequence (FIG. 2B, compare lane 2 with lane 1), or when the MS2 binding site contained a single point mutation that reduces binding by 3000-fold (FIG. 2B, compare lane 6 with lane 5). The compilation of the effect at various positions is shown in FIG. 2C where the GST-MS2-mediated change in the relative level of distal/proximal use is plotted. The largest effect was observed when the MS2 binding site was located 26 and 37 nt upstream of the 5' splice junction. The insertion of the MS2 binding site at similar distances downstream from the 5' splice junction had no effect. Thus, the binding of a GST-MS2 protein in the vicinity of a 5' splice site can decrease splicing at that site. Splicing interference by GST-MS2 is position-dependent since binding 42 to 16 nt upstream of the targeted 5' splice site affected splice site use, whereas essentially no effect was detected when binding occurred 17 to 42 nt downstream of the splice junction. The local structure surrounding a binding site for MS2 may alter the affinity of GST-MS2. The GST-MS2 protein can therefore recapitulate the activity of factors that bind upstream of a 5' splice site to obstruct its use. Because the spliceosome occupies a similar space downstream from the splice junction, it is unclear why the binding of GST-MS2 at equivalent positions downstream from the 5' splice site had no effect on splice site selection. The asymmetric impact of protein binding near a 5' splice site may reflect intrinsic preferences in the ability of the spliceosome to deal with structural impediments.

Figure 3A:
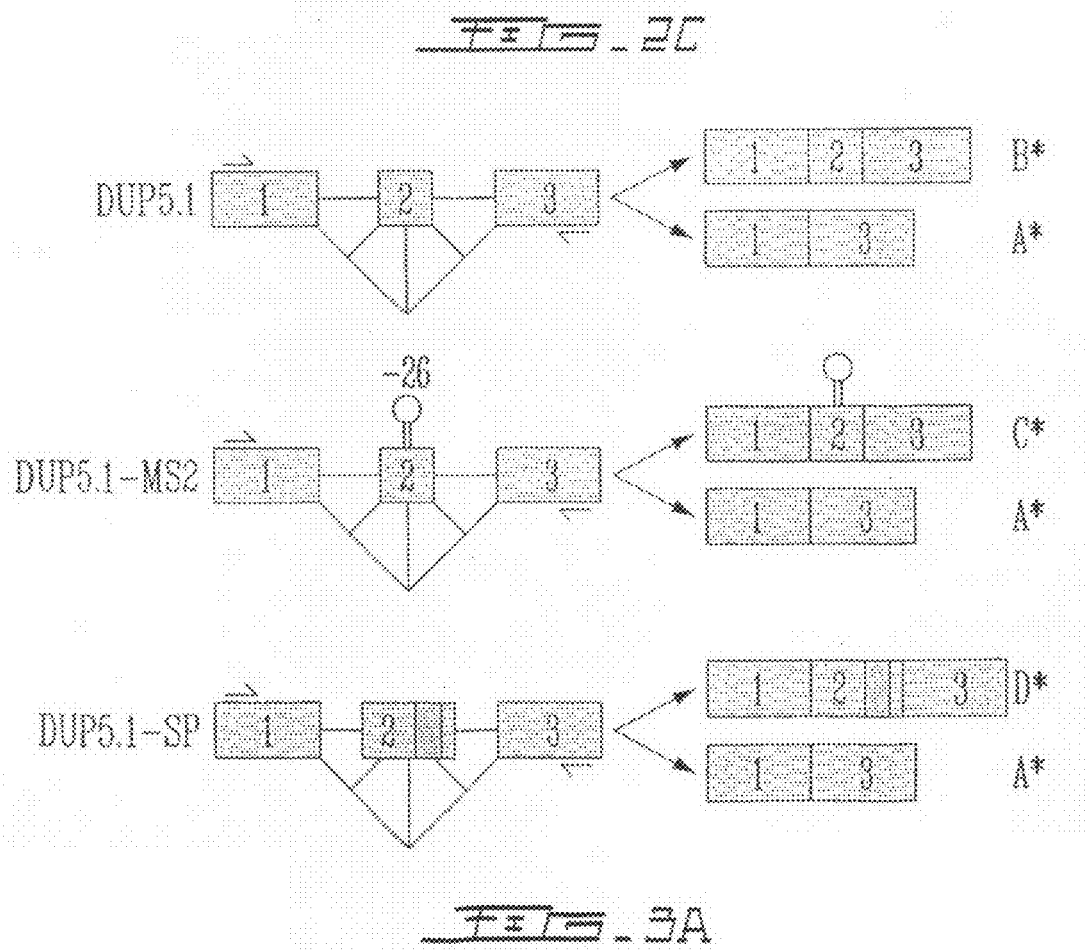

To ascertain whether the interference detected in vitro could also be observed in vivo, the β-globin DUP5.1 reporter plasmid was used. The internal exon 2 in DUP5.1 is preferentially excluded because of its small size, and its inclusion level did not change upon co-expression of GST-MS2 (FIG. 3B, lanes 1-2). Insertion of the MS2 binding site or a spacer element 26 nt upstream of the 5' splice junction increased the size of the central exon leading to almost complete inclusion of the central exon (FIG. 3B, lanes 3 and 5). Co-transfection with the GST-MS2 expression plasmid promoted a decrease in the frequency of exon 2 inclusion only when DUP5.1 contained the MS2 binding site (FIG. 3B, lane 6). This result shows that targeting the binding of a protein upstream of a 5' splice site can interfere with splicing in vivo.

Example 3

Figure 4B:
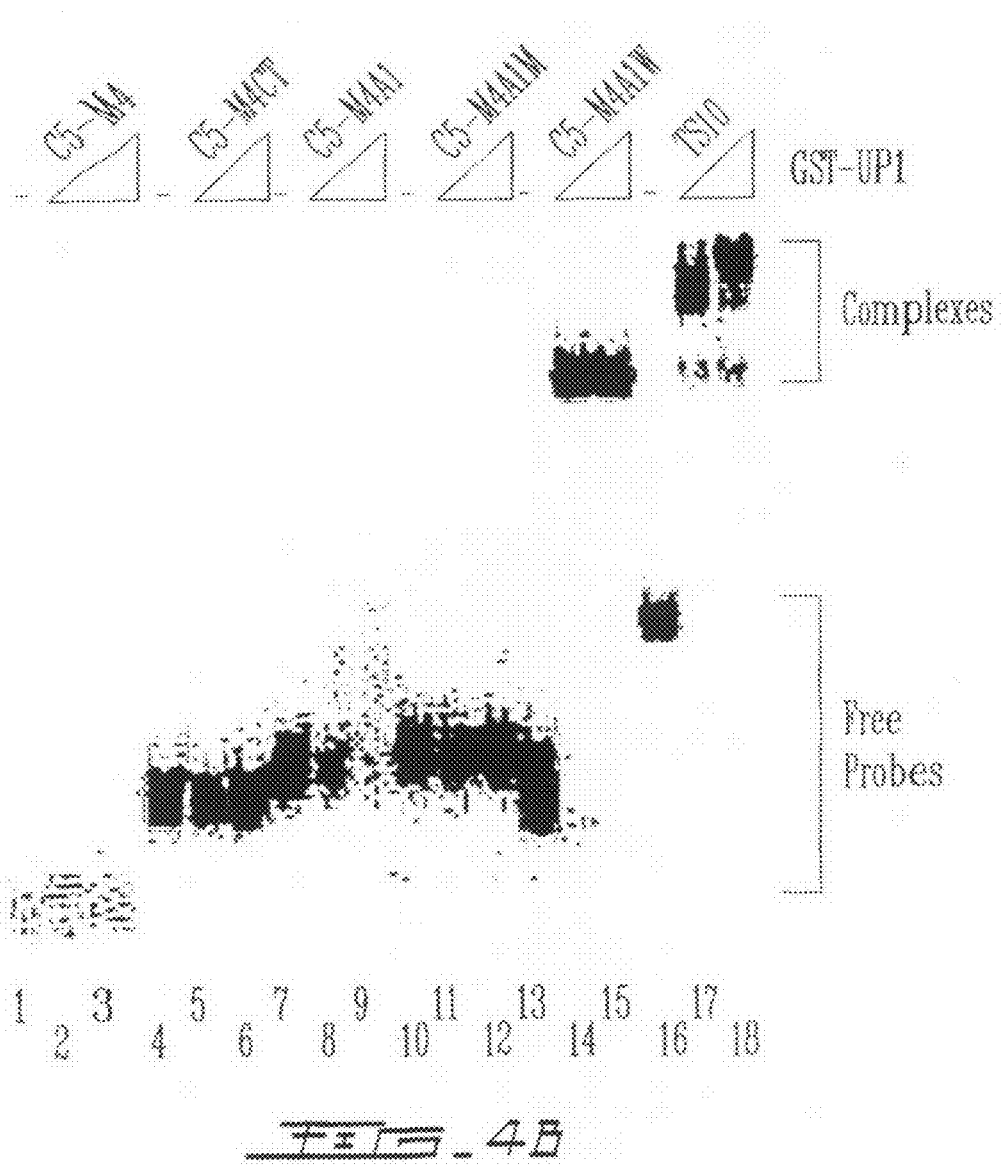
Figure 4E:
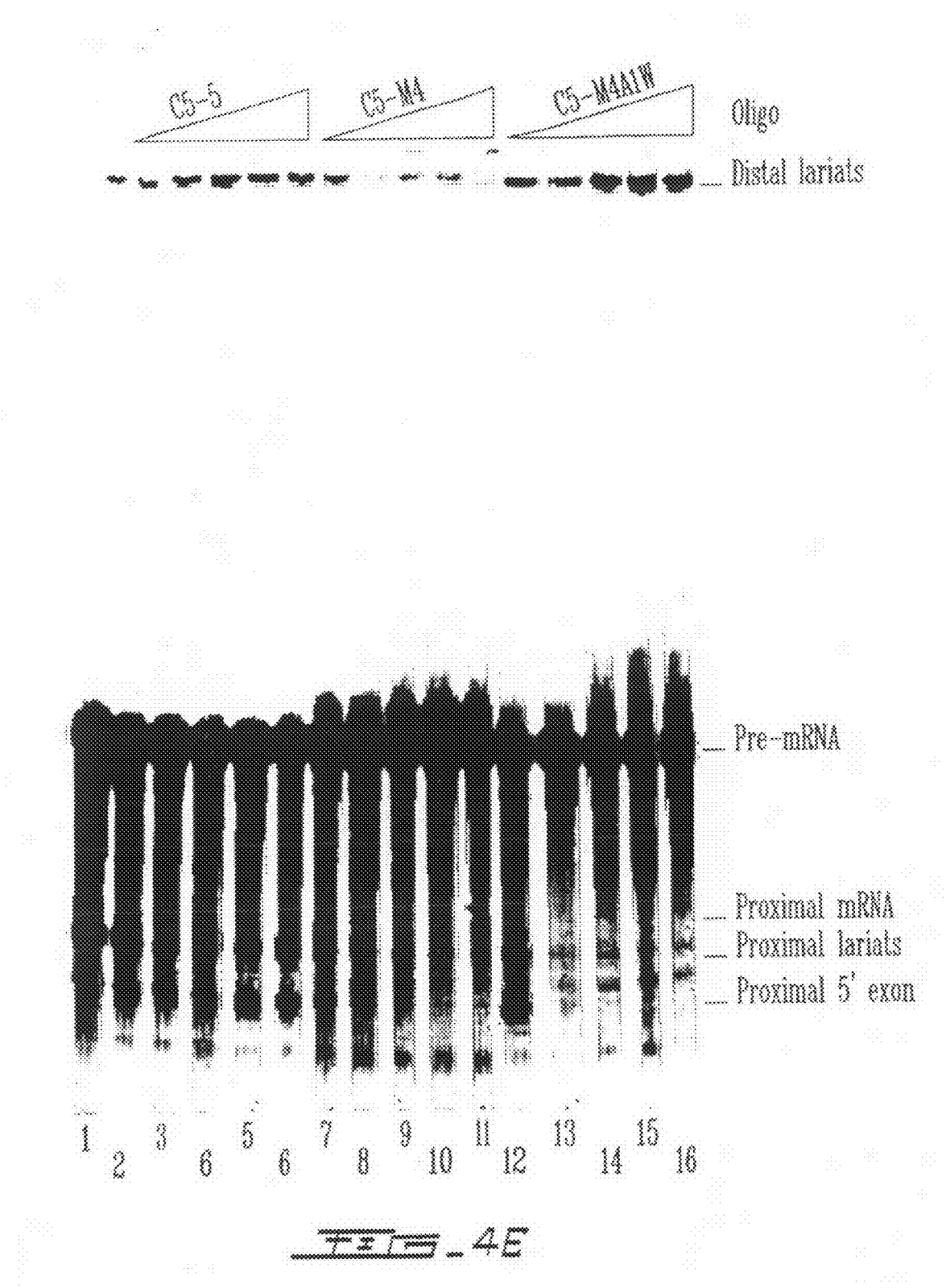

Effects of Targeted Protein Binding Ln Trans on Splice Site Interference In Vitro The applicants also determined that targeting protein binding to promote interference did not require that the binding site be present in cis (i.e., on the pre-mRNA itself). Indeed, the binding site was effective when provided in trans using an oligonucleotide that contains the protein binding site and a portion complementary to the target sequence. A series of antisense oligos complementary to a portion of the C5'-/- pre-mRNA −4 to −23 upstream of the proximal 5' splice site (FIG. 4A) was designed. The C5-M4A1 oligo contains a 16 nt-long non-hybridizing 5' extension made of DNA and carrying one high-affinity binding site for the hnRNP A1/A2 proteins (TAGGGA). The C5-M4A1W contains the winner RNA sequence for optimal hnRNP A1 binding. A mutated version of this oligo (C5-M4A1M) harboring two GGG to CGC mutation was used as a control. Oligos carrying a non-related 16 nt-long tail (C5-M4CT) or lacking a tail (C5-M4) were also used as controls. All oligos were tested for binding by the UP1 protein, a shortened derivative of hnRNP A1 (FIG. 4B). Complex formation in a native gel indicated that UP1 bound best to C5-M4A1W followed by C5-M4A1. The mutated C5-M4A1W was not bound by UP1 nor were the control oligos C5-M4 and C5-M4CT. Splicing assays were next carried out to investigate the interfering capacity of these oligos. The hybridization of the C5-M4 oligo was sufficient to provoke a reduction in the use of the proximal 5' splice site such that splice site selection shifted from predominantly proximal to nearly equivalent use of each 5' splice site (FIG. 4C, lanes 2-4). A similar effect was obtained with the C5-M4CT and the C5-M4A1M oligos (FIG. 4C, lanes 8-10 and 14-16, respectively). For C5-M4, C5-M4CT and C5-M4A1M, the ratio of distal to proximal products was shifted from 0.25 to 1.3. Thus, the presence of a nucleic acid extension emerging at position −4, relative to the 5' splice junction, does not offer more inhibitory activity than a duplex covering positions −4 to −23. A stronger shift was obtained with the C5-M4A1 (FIG. 4C, lanes 5-7 and FIG. 4D). The strongest shift was observed with the C5-M4A1W oligo which elicited the largest reduction in proximal 5' splice site use and the biggest increase in distal 5' splice site use (FIG. 4C, lanes 11-13 and FIG. 4D). The amplitude of shift obtained in this case was 30-fold at the highest concentration of C5-M4A1W oligos. These results indicate that a 5' tail carrying A1/A2 binding sites adds considerably to the interfering capability of the oligo leading to more efficient use of the competing distal 5' splice site. The activity of the interfering oligo carrying the A1 binding tail was also compared with the activity of an oligo directly complementary to the proximal 5' splice site (C5-5). Surprisingly, the C5-M4A1W oligo was more efficient than the C5-5 oligo at eliciting a shift toward the distal 5' splice site (FIG. 4E, compare lanes 2-6 with lanes 12-16). Finally, the effect of positioning A1 further upstream was tested by using an oligo (C5-M26A1) that hybridizes −26 to −45 nt upstream of the 5' splice site of exon 7B. Compared to an oligo that only forms a duplex with this region (C5-M26), the protein-bound C5-M26A1 oligo had a smaller impact on 5' splice site selection than C5-M4A1 (FIG. 4F, compare lanes 5-7 with lanes 11-13). Thus, the position of the A1-binding tail relative to the 5' splice site is important for activity.

Example 4

Modulation of Bcl-X Alternative Splicing by Protein-Binding Oligos in Cells

On several occasions, the Bcl-x pre-mRNA has been a target for splice site modulation by duplex-forming oligos. Two types of oligos have been used: one that targets directly the proximal 5' splice site of Bcl-xL (positions +2 to −16 relative to the 5' splice junction), the other was complementary to positions 16 to 35 nt upstream of the same 5' splice site. Each oligo has been reported to block Bcl-xL splicing, such that the relative abundance of the isoforms shifts from almost exclusively Bcl-xL to predominantly Bcl-xS. To determine the modulating efficiency of protein-binding oligos, a series of 2'O-Me oligonucleotides was transfected in cells. The oligos used are listed in Table 1. X-5 is complementary to the 5' splice site of Bcl-xL (+7 to −13); X-M4 is complementary to the −4 to −23 region upstream of the Bcl-xL site. The other two oligos contain the same complementary region and carry a 5' tail carrying two high-affinity binding sites for hnRNP A1 or a mutated version (X-M4A1W and X-M4A1M, respectively). FIG. 5A shows the splicing map of the Bcl-x pre-mRNA illustrating the splicing events leading the Bcl-xL and Bcl-xS mRNA producing. The A1 binding ability of these 2'O-Me oligos was confirmed by gel shift assays (FIG. 5B). The best UP1 binder was X4-A1W (lanes 7-9), whereas no binding was detected using X-M4A1W, X-M4 and X-5. Transfection of the individual oligo was carried out in triplicates at different concentrations (25, 50 and 100 nM) in the prostate carcinoma cell line PC-3, the colon carcinoma cell line HCT 116 and the breast carcinoma cell line MCF-7 using as a control transfection with oligofectamine alone or with an unrelated oligo (C-RNA). Twenty-four hours post-transfection, RNA was extracted and analyzed by RT-PCR to monitor changes in the relative abundance of the Bcl-xL and Bcl-xS mRNAs. Compared to the control, the X-5 oligo had little activity at all concentrations tested in PC3, HCT 116 and MCF-7 cells (FIG. 5C, lane 2; FIG. 5D, lane 3 and FIG. 5E, lane 3). The duplex-forming X-M4 oligo displayed moderate shifting ability in all cell lines (FIG. 5C, lane 3; FIG. 5D. lane 4 and FIG. 5E, lane 4). The X-M4A1W oligo elicited the strongest shift toward the production of the Bcl-xS form with an efficiency that was clearly superior to the effect observed with X-M4 in all cell lines (FIG. 5C, lane 4; FIG. 5D. lane 5 and FIG. 5E, lane 5). This level of shift is among the strongest that has been reported for Bcl-x. As expected, the X-M4A1M oligo was considerably less efficient (FIG. 5C, lane 5; FIG. 5D. lane 6 and FIG. 5E, lane 6), thus supporting the conclusion that A1/A2 binding is important for the activity of the interfering oligo. The residual activity may reflect low affinity binding by A1/A2 or may indicate that a 5' tail can display intrinsic interfering activity in vivo.

To assess the role of hnRNP A1/A2 proteins in the activity of the X-M4A1W oligo, an RNA interference experiment using siRNAs against hnRNP A1/A2 was carried out in HeLa S3 cells (FIGS. 6A-B). siRNAs and interfering RNA oligos were co-transfected and total RNA was extracted 24 h later. Parallel transfections were continued for 96 h at which time proteins were extracted and analyzed by western analysis. The level of A1/A2 proteins was reduced to represent less than 25% of the level observed in mock-treated cells. RT-PCR analysis of the Bcl-x expression levels indicated that the X-M4A1W oligo shifted splicing toward Bcl-xS production in HeLa S3 cells (FIG. 6B, compare lane 5 with lane 1). The duplex-forming X-M4 oligo had little activity (FIG. 6B, lane 3). Notably, the activity of the X-M4A1W oligo was impaired when the cells had been co-transfected with siRNAs against A1/A2 (FIG. 6B, lane 6), indicating that hnRNP A1/A2 proteins are required for the in vivo activity of the X-M4A1W oligo.

Positioning a protein in the vicinity of a 5' splice site either directly or through the use of an antisense oligo reduces splicing at this site. This effect is presumed to be caused by an interference with splice site recognition or with spliceosome assembly. To confirm this mechanism of action, an oligonucleotide-mediated RNAse H cleavage assay was performed. In this assay, a DNA oligo complementary to the targeted 5' splice site is added to a splicing mixture along with RNAse H which degrades the RNA portion of the RNA/DNA duplex. Protection are time 0 is indicative of U1 snRNP binding, While the protection observed following incubation at 30° C. indicates that U1 snRNP-dependent spliceosomal complexes have assembled onto the 5' splice site. A protection assay was performed on the C5-M26S and C5'-/- pre-mRNAs using a DNA oligo complementary to the 5' splice site of exon 7B (FIG. 7A and FIG. 7B, respectively). In the absence of GST-MS2 protein or interfering oligos, protection is observed at time 0 and this protection increased upon incubation at 30° C. (FIG. 7A and FIG. 7B, lanes 1-3). The bulk of this protection was U1 snRNP-dependent because protection was greatly decreased when the assay was performed in an extract in which the 5' end of U1 snRNA had been degraded previously (FIG. 7A, lanes 7-9). The addition of GST-MS2 protein decreased protection at time 0 and later time points following incubation at 30° C. (FIG. 7A, lanes 4-6), suggesting that the binding of U1 snRNP and U1-snRNP-dependent complexes was compromised. It was noted that the C5-M4 oligo had little effect on the protection observed at time 0, but a stronger effect on the protection following incubation at 30° C. (FIG. 7B, lanes 4-6), indicating that the oligo was interfering mainly with the assembly of U1 snRNP-dependent splicing complexes. In contrast, the C5-M4A1W oligo almost completely eliminated early and late protections (FIG. 7B, lanes 7-9), consistent with the conclusion that this oligo prevents the initial binding of U1 snRNP.

Thus, it was shown that this approach is efficient in vitro and in vivo. In vitro, shifting 5' splice site use with protein-binding RNA oligo works best with oligo containing several binding sites for hnRNP A1/A2 proteins. These sites should emerge from the duplex portion and be directly interfering with 5' splice site recognition. Surprisingly, the splicing shifts obtained with protein-binding oligos carrying A1/A2 binding sites were even more important than the shift obtained with an oligo complementary to the 5' splice site itself. In vivo, protein-binding 2'O-Me oligos carrying binding sites for A1/A2 were also very active on a Bcl-x pre-mRNA and greatly superior in activity to oligos complementary to the 5' splice site or to an oligo that only formed a duplex upstream of that 5' splice site. An additional tail that was similarly active carried a branchsite region which may be bound by mBBP/SF1 or U2 snRNP. The greater activity of tailed oligos relative to oligos directly complementary to 5' splice sites is striking. Because 5'splice sites conform' to a consensus, these results could be explained, at least in part, if the oligo complementary to the 5' splice site has some affinity for 5' splice sites in other pre-mRNAs, thereby reducing the effective concentration of the oligo for the intended target. Moreover, if this is the case, the hybridization of this oligo to other related 5' splice sites may have secondary effects. Indeed, an oligo complementary to the 5' splice site of a β-globin pre-mRNA can alter the expression of may genes, although it is not known to what extent this effect occurs via alterations in splicing. Thus, the use of oligos complementary to exonic sequences may improve their specificity of action, but duplex formation near but not including a 5' splice site should be less active because they are at a distance from the 5' splice site. It was shown herein that duplex formation in that region does not prevent the initial binding of U1 snRNP to the 5' splice site, but reduces later U1-dependent complex assemblies. Potency can however be increased greatly by providing an extension that constitutes a binding site(s) for hnRNP A1/A2 proteins. Such a tail reduces the initial binding to the target 5' splice site.

These results showed a more general applicability of this method for splice site selection interference by circumventing the need for the addition of a purified protein. Furthermore, this method can be used with an oligonucleotide carrying binding sites for any of a variety of proteins including single-stranded or double-stranded DNA or RNA binding proteins including, but not limited to, SR family proteins, hnRNP proteins, U2AF, and TAR proteins.

Example 5

High-Affinity A1/A2 Binding Sites Stimulate the Splicing of Long Introns

As an experimental system to study the contribution of hnRNP A/B binding sites (ABS), a model pre-mRNAs containing portions of exon 7 or exon 7B of the hnRNP A1 gene paired with the adenovirus L2 exon (7-Ad and 7B-Ad; FIG. 8A) was used. Co-incubation of these two model pre-mRNAs carrying short introns (each at a concentration of 80 pM) for different periods in a HeLa nuclear extract indicated that they were spliced with similar efficiencies, as determined by RT-PCR analysis (FIG. 8B, lanes 1-6). The RT-PCR assay was performed in conditions that displayed a linear relationship between the amounts of input RNA and amplified products over a large range of input RNA concentrations (from 10-fold less to at least 6-fold more than the amounts used in the assays). To test the effect of intron length on splicing efficiency, a 1015 nt-long lambda fragment, insert A, was inserted into the intron of both model pre-mRNAs. Following incubation of these pre-mRNAs (7-AdA and 7B-AdA), a RT-PCR assay was performed to amplify splicing products. In comparison with the short-intron 7-Ad and 7B-Ad pre-mRNAs, the splicing efficiencies of the long-intron pre-mRNAs were reduced approximately 8-fold (FIG. 8B, lanes 7-12 and accompanying graph). Two different lambda sequences were also tested in the context of the 7-Ad pre-mRNA (7-AdB and 7-AdC pre-mRNAs with a 943 nt and a 1038 nt insert, respectively). In this experiment, a short-intron 7B-Ad pre-mRNA was co-incubated with each of the long-intron pre-mRNAs. The RT-PCR analysis indicated that the production of spliced products from long-intron substrates was also impaired (FIG. 8C, lanes 2-6). Thus, increasing intron size with lambda sequences strongly reduces splicing efficiency.

To determine whether high-affinity A/B binding sites (ABS) could stimulate the splicing of long introns, ABS was inserted in the long-intron pre-mRNA substrates. The ABS site corresponds to the CE1a element identified in the mouse hnRNP A1 pre-mRNA. One ABS was inserted 26 nt downstream from the 5' splice junction and a second ABS was inserted 88 nt upstream from 3' splice junction (FIG. 8A). The presence of ABS in the 7-AdA and 7B-AdA pre-mRNAs stimulated splicing approximately 4-fold (FIG. 8B, lanes 13-18 and accompanying graph). Likewise, the presence of ABS in 7-AdB and 7-AdC pre-mRNAs stimulated splicing 3 to 5-fold (FIG. 8C, lanes 7-11). It has been shown previously that inverted repeats mimics the activity of ABS in 5' splice site selection assays, providing support for the looping out model of A1 action. The insertion of 20 nt-long inverted repeats in place of ABS also stimulated long-intron splicing in vitro (FIG. 8C, lanes 12-16). The level of stimulation obtained with inverted repeats was generally superior to the level obtained with ABS.

ABS can therefore stimulate the splicing of pre-mRNAs carrying different intron sequences and different 5' splice sites. To test whether ABS also worked on a different 3' splice sites, pre-mRNAs carrying the 3' splice site and a portion of Bcl-X exon 3 (7-BclA and 7B-BclA) were used. The presence of ABS strongly stimulated the splicing of 7-BclA (FIG. 8D, compare the 7/Bcl product in lanes 1-7 with lanes 8-12). A similar but less important stimulation was noted with the 7B-BclA pre-mRNA. The effect of inserting only one ABS was also tested. Notably, one ABS at the upstream or downstream position yielded an intermediate level of stimulation for the 7-AdA pre-mRNA (FIG. 9, lanes 9-16). In contrast, a single ABS upstream in the 7-AdB pre-mRNA was more active than an ABS at the downstream position.

To confirm a role for the hnRNP A/B proteins in the stimulation of long-intron splicing, increasing amounts of a DNA oligonucleotide (TS10) carrying vertebrate telomeric sequences which represent high-affinity binding sites for A1 and A2 (apparent Kd below 5 nM) were added to a HeLa nuclear extract. It has been shown that an excess of TS10 abrogates the activity of ABS in a 5' splice site selection assay. Adding an excess of TS10 similarly abolished the stimulation of splicing associated with the presence of ABS in the long intron of 7-AdB, without affecting the splicing efficiency of the short-intron pre-mRNA (FIG. 10A, lanes 6-10). Notably, the addition of TS10 also reduced the basal level of splicing for a long-intron pre-mRNA lacking ABS (lanes 1-5), showing that A/B proteins contribute to the splicing of this long intron even in the absence of added ABS. This conclusion was confirmed by increasing the level of hnRNP A1 in the extract using recombinant GST-A1 protein. Whereas the addition of A1 did not alter the splicing efficiency of short-intron 7B-Ad pre-mRNA, it stimulated the splicing of the 7-AdB pre-mRNA (FIG. 10B, lanes 1-4). Recombinant A1 also stimulated the splicing efficiency of a 1 ng-intron pre-mRNA carrying ABS (FIG. 10B, lanes 5-8), but no stimulation was observed when A1 was added to a long-intron pre-mRNA which was already spliced efficiently through the use of inverted repeats (lanes 9-12). Because the GST moiety may foster protein dimerization, His-tagged A1 were relied on to carry out the supplementation experiment. As shown in FIG. 10C, His-A1 was as active as GST-A1 at stimulating long-intron splicing. These results are consistent with the notion that bound A1 molecules loop out portions of intron to stimulate commitment between distant splicing partners.

Example 6

Protein-Binding Oligonucleotides Carrying ABS Stimulate Long Intron Splicing In Vitro If an interaction between bound hnRNP A/B proteins is responsible for the activity of ABS, providing ABS in trans using protein-binding oligonucleotides may be compatible with activity. To test this, RNA oligonucleotides carrying a portion complementary to intron regions and a non-hybridizing portion formed by the ABS (FIG. 11A) were designed. In a HeLa extract, the 7-AdA and 7B-AdB pre-mRNAs were incubated with a pair of RNA oligonucleotides; UA and Da each containing an ABS and a sequence complementary to the upstream and the downstream portion of the intron in 7-AdA and 7B-AdA pre-mRNAs. Notably, the addition of the oligonucleotide mixture (160 nM of each oligonucleotide) stimulated 7/Ad and 7B/Ad splicing (FIG. 11B, lanes 1-6 and lanes 10-12, respectively). The same mixture of oligonucleotides added to the 7-AdB pre-mRNA did not stimulate splicing (lane 8). In general, concentrations of oligonucleotides varying between 0.08 to 160 nM were sufficient to observe stimulation of splicing (representing a molar excess of 10 to 2000-fold relative to the pre-mRNA). The level of stimulation varied between 2 to 8-fold between different experiments. Concentrations superior to 160 nM usually promoted a reduction in splicing efficiency of large introns, without affecting short-intron splicing, possibly because of titration of hnRNP A/B proteins by an excess of oligonucleotides.

Figure 11A:
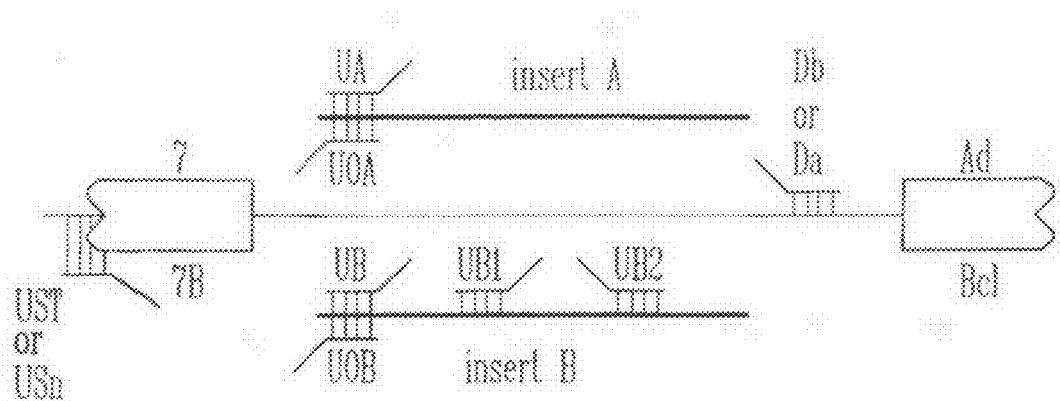
Figure 11B:
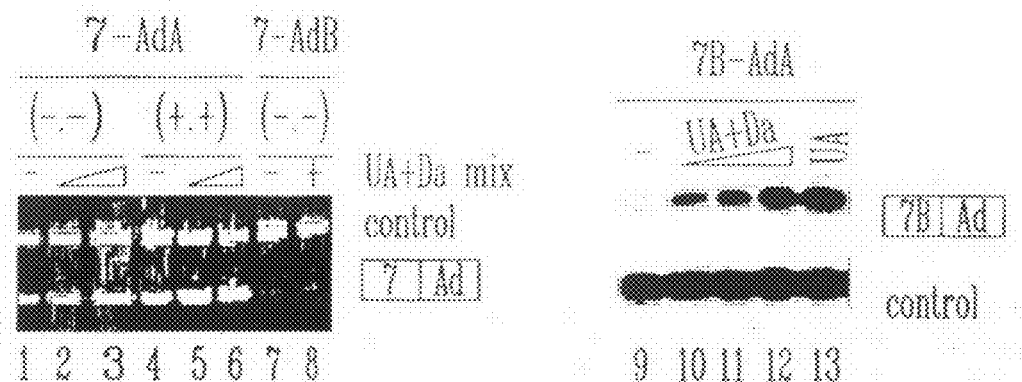
Figure 11C:
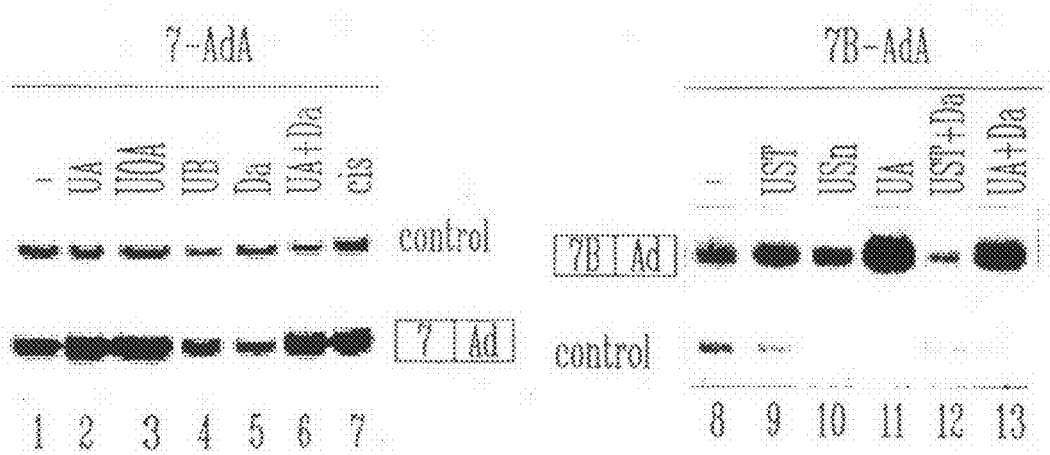

The effect of providing a single ABS at the upstream or the downstream position using protein-binding oligonucleotides was also investigated. Using the 7-AdA pre-mRNA, it was noted that the upstream UA oligonucleotide alone was nearly as active as when both ABS were provided in trans (FIG. 11C, compare lane 2 with lane 6, and see the accompanying graph for quantitation). In contrast, the downstream Da oligonucleotide did not stimulate splicing (FIG. 11C, lane 5). Notably, the position of the A/B binding extension on the upstream oligonucleotide was not important since ABS tails located at the 5' end or the 3' end of the oligonucleotide were equally effective (FIG. 11C, lanes 2 and 3). An upstream oligonucleotide lacking complementarity to the pre-mRNA did not stimulate long-intron splicing (FIG. 11C, lane 4), but the same oligonucleotide hybridizing to the 7-AdB pre-mRNA stimulated splicing of this pre-mRNA (FIG. 11D, lane 2). Moreover, an oligonucleotide hybridizing to the same site in 7-AdB but carrying a non-ABS extension did not stimulate splicing (FIG. 11D, lane 3), demonstrating that duplex formation near the 5' splice site does not stimulate splicing.

Stimulation of splicing by protein-binding oligonucleotides was also observed with other pre-mRNAs. In the case of 7B-BclA, only the pair of oligonucleotides UA and Db were active (FIG. 11E, lanes 2-6) and oligonucleotides that hybridized at the upstream or the downstream position alone did not stimulate splicing (lanes 7 and 9, respectively). In contrast, the oligonucleotide upstream alone (UB) stimulated splicing of the 7-BclB pre-mRNA as efficiently as the pair, whereas the downstream oligonucleotide Db offered no stimulation (FIG. 11F). As expected, oligonucleotides UA and Da, which stimulated 7-AdA pre-mRNA splicing, were inactive with the 7-BclB pre-mRNA (FIG. 11F, lane 8). Thus, while splicing of pre-mRNAs carrying the 3' splice site of the adenovirus L2 exon was always stimulated by the upstream oligonucleotide alone, this behavior in pre-mRNAs carrying the Bcl-X 3' splice site varied with the nature of the intron sequences.

Example 7

Protein-Binding Oligonucleotides Carrying A1/A2 Binding Sites can Also Promote Alternative Splicing Intronic high-affinity ABS were initially characterized as capable of affecting 5' splice site selection. To test whether protein-binding oligonucleotides could also promote shifts in 5' splice site utilization, a model pre-mRNA carrying the 5' splice site of exons 7 and 7B in competition for the unique 3' splice site of the adenovirus exon L2 was used. On a similar pre-mRNA, it has been shown previously that cis-acting ABS downstream of both 5' splice sites can shift 5' splice site utilization from almost exclusively proximal (internal) to almost exclusively distal (external). A single ABS inserted either downstream, of either 5' splice site also shifted splicing to the distal site, albeit to a lesser extent. The addition of a mixture of protein-binding RNA oligonucleotides complementary to regions downstream from the distal 5' splice site and upstream from the 3' splice site also promoted a strong shift towards the use of that site (FIG. 12, lanes 2-6). Notably, the addition of the upstream oligonucleotide alone was as efficient as the pair (FIG. 12, lane 7) and the downstream oligonucleotide alone had no activity (FIG. 12, lane 9). The addition of an upstream oligonucleotide bearing a non-ABS tail did not stimulate splicing (FIG. 12, lane 8). Likewise, the addition of a mixture of oligonucleotides that contain ABS but cannot hybridize to the pre-mRNA did not alter 5' splice site usage (FIG. 12, lane 10). These results confirm the role of ABS in alternative splicing and further support to the view that A/B proteins remodel pre-mRNA structure to favor the use of the distal 5' splice site.

It has been shown that protein-binding RNA oligonucleotides can be used not only to stimulate the splicing of long introns but also to modulate 5' splice site selection. Complementary oligonucleotides have been used for some times in strategies aimed at preventing splice site usage by directly covering the target splice site or its immediate surroundings. More recently, bifunctional RNA or PNA oligonucleotides have been used to recruit SR proteins (Skordis, 2003) or provide direct activating function (Cartegni, 2003), respectively. The approach described here offers additional flexibility in the choice of the strategy to influence alternative splicing. This approach may be applicable to situations whose goal is to promote exon skipping or to prevent the use of an aberrant 5' splice site. In these cases, providing ABS on each side of the target splice site(s) may decrease its use. On the other hand, increasing the size of introns flanking an alternative exon favors exon skipping {Bell, 1998}, and providing ABS in a long intron next to an alternative exon should facilitate exon inclusion. These approaches could also be applied towards the modulation of alternative splicing in vivo with the goal of understanding the function of spliced isoforms. Additional strategies using hnRNP A/B-bound oligonucleotides can also be developed to influence or correct the aberrant splicing associated with human diseases.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method of repressing the use of a splice site of a target pre-mRNA molecule, said method comprising forming a complex between an oligonucleotide, said target pre-mRNA molecule and a hnRNP protein in a cell or a cell extract, wherein said oligonucleotide comprises at least two different sequence elements:
   (i) a single stranded RNA having between 18 and 20 nucleotides and being complementary to a region upstream of said splice site in said target pre-mRNA molecule, said region being located between said splice site and 46 nucleotides upstream of said splice site; wherein the 5' end of said single stranded RNA is operatively linked to
   (ii) a single stranded nucleic acid extension having between 16 and 20 nucleotides and containing a hnRNP protein binding site sequence element for binding said hnRNP protein.

2. The method of claim 1, wherein said splice site is a 5' splice site.

3. The method of claim 1, wherein said spice site is a 3' splice site.

4. The method of claim 1, wherein said cell is a mammalian cell.

5. The method of claim 1, wherein the protein is a hnRNP A1/A2 protein.

6. The method of claim 1, wherein the single stranded nucleic acid extension is a single stranded RNA.

* * * * *